United States Patent [19]

Emonds-Alt et al.

[11] Patent Number: 5,618,938
[45] Date of Patent: Apr. 8, 1997

[54] PROCESS FOR PREPARING STEREO ISOMERS OF NEUROKININ RECEPTOR ANTAGONISTS

[75] Inventors: Xavier Emonds-Alt, Combaillaux; Pierre Goulaouic, Montpellier; Vincenzo Proietto, Saint Georges D'Orques; Didier Van Broeck, Murviel les Montpellier, all of France

[73] Assignee: Sanofi, Paris, France

[21] Appl. No.: 479,634

[22] Filed: Jun. 7, 1995

Related U.S. Application Data

[62] Division of Ser. No. 208,672, Mar. 11, 1994, which is a division of Ser. No. 610,093, Nov. 5, 1990, Pat. No. 5,317,020.

[30] Foreign Application Priority Data

Nov. 6, 1989 [FR] France .................. 89 14517
Jun. 15, 1990 [FR] France .................. 90 07534

[51] Int. Cl.$^6$ .................. C07D 211/06; C07D 405/00
[52] U.S. Cl. .................. 544/360; 544/364; 544/365; 544/366; 544/367; 544/374; 544/376; 544/379; 544/386; 544/391; 544/394; 544/398; 544/399; 546/186; 546/189; 546/190; 546/193; 546/194; 546/198; 546/205; 546/209; 546/210; 546/212; 546/213

[58] Field of Search .................. 544/360, 364, 544/365, 366, 367, 374, 376, 379, 386, 391, 394, 398, 399; 546/186, 189, 190, 193, 194, 198, 205, 209, 210, 212, 213

[56] References Cited

U.S. PATENT DOCUMENTS

| | | | |
|---|---|---|---|
| 3,941,795 | 3/1976 | Carr et al. | 546/205 |
| 4,059,621 | 11/1977 | Vincent et al. | 564/180 |
| 4,485,108 | 11/1984 | Jozic | 546/205 |
| 4,559,349 | 12/1985 | Storni | 546/233 |
| 4,916,156 | 4/1990 | Mosse et al. | 514/510 |
| 4,942,169 | 7/1990 | Sugimoto et al. | 546/233 |

FOREIGN PATENT DOCUMENTS 0288352 10/1988 European Pat. Off. .

OTHER PUBLICATIONS

Decarie et al., "Characterization of the peripheral action of neuropeptide K on the rat cardiovascular system", *European Journal of Pharmacology*, 213: 125–131 (1992).
Takano et al., "Role of NK-1 receptor in central cardiovascular regulation in rats: studies on a novel non-peptide antagonist, CP-96,345, of substance P NK-1 receptor", *Neuroscience Letters* 139: 122–125 (1992).
Frossard et al., "Minireview—Tachykinin Receptors and the Airways", *Life Sciences* 49: 1941–1953 (1991).

Fleetwood–Walker et al., "The involvement of neurokinin receptor subtypes in somatosensory processing in the superficial dorsal horn of the cat", *Brain Research* 519: 169–182 (1990).
Lam et al., "Inhibition of carrageenan induced inflamation in the rat knee joint by substance P antagonist", *Annals of the Rheumatic Diseases* 48: 928–932 (1989).
Lotz et al., "Substance P Activation of Rheumatoid Synoviocytes: Neural Pathway in Pathogenesis of Arthritis", *Science, Reports* 235: 893–894 (1987).
McGillis et al., "Substance P and immunoregulation", *Federation Proc.*, 46: 196–199 (1987).
Giuliani et al., "$NK_2$ tachykinin receptors and contranction of circular muscle of the human colon: characterization of the $NK_2$ receptor type", *European Journal of Pharmacology* 203: 365–370 (1991).
Advenier et al., "Relative potencies of neurokinins in guinea pig traches and human bronchus", *European Journal of Pharmocology* 139: 133–137 (1987).
Le Gall et al., "Disubstituted amino alcohols of the omega-aminopentanol, –hexanol and –heptanol series", *Chemical Abstracts* 72: 385 43014m (1970).
R. Robin, "Five–membered nitrogen heterocycles", *Chemical Abstracts* 73: 344 76968z (1970).
Volkova et al., "3–Phenylpyrrolidine", *Chemical Abstracts* 78: 400 159420u (1973).
Dobrina et al., "Synthesis and study of adrenolytic substances. IV. Pyrroxan and related compounds", *Chemical Abstracts* 81: 458 91445k (1974).
Miyake et al., "Synthesis of 4–substituted isochroman derivatives", *Chemical Abstracts* 97: 820 215838t (1982).
Miyake et al., "Synthesis of 4–substituted 1,2,3,4–tetrahydroisoquinoline derivatives", *Chemical Abstracts* 98: 401 4469f (1983).
Annex "Acetamide, N–(2–3thyl–5–hydroxy–2–phenylpentyl)", *Chemical Abstracts* 5: 38504p (1990).
Kobayashi et al., "Studies on the synthesis of antiulcer agents. I. Synthesis and antiulcer activity of imide derivatives", *Chemical Abstracts* 101: 763 230442d (1984).

*Primary Examiner*—C. Warren Ivy
*Assistant Examiner*—Raymond Covington
*Attorney, Agent, or Firm*—Foley & Lardner

[57] ABSTRACT

Compounds of the formula $$Ar-C(X)(X')-Y-[\text{ring}]-N-(CH_2)_m-C(Q)(Ar')-CH_2-N(R)-T-Z \quad (I)$$

and their salts with mineral or organic acids are useful as neurokinin receptor antagonists. Methods of preparing the compounds, especially pure STEREO ISOMERS thereof, are provided.

1 Claim, No Drawings

PROCESS FOR PREPARING STEREO ISOMERS OF NEUROKININ RECEPTOR ANTAGONISTS

This application is a divisional of application Ser. No. 08/208,672, filed Mar. 11, 1994 which is a divisional application of U.S. Ser. No. 07/610,093, filed Nov. 5, 1990, now U.S. Pat. No. 5,317,020.

The present invention relates to novel aromatic derivatives substituted by an amino group and by various ester, amine or amide functional groups, and to their enantiomers.

The present invention further relates to the method of obtaining the compounds, which can be enantioselective, and to the use of the compounds according to the invention in compositions for therapeutic use and more particularly in pathological phenomena involving the neurokinin system, such as: pain (D. REGOLI et al., Life Sciences, 1987, 40, 109–117), allergy and inflammation (J. E. MORLAY et al., Life Sciences, 1987, 527–544), circulatory insufficiency (J-LOSAY et al., 1977, Substance P, Von Euler, U.S. and Pernow ed., 287–293, Raven Press, New York), gastrointestinal disorders (D. REGOLI et al., Trends Pharmacol. Sci., 1985, 6, 481–484) and respiratory disorders (J. MIZRAHI et al., Pharmacology, 1982, 25, 39–50).

Ligands endogenous to neurokinin receptors have been described, such as substance P (SP), neurokinin A (NKA) (S. J. BAILEY et al., 1983, Substance P, P. Skrabanek ed., 16–17 Boole Press, Dublin) and neurokinin B (NKB) (S. P. WATSON, Life Sciences, 1983, 25, 797–808).

Neurokinin receptors have been recognized on numerous preparations and are currently classed in three types: $NK_1$, $NK_2$ and $NK_3$. Whereas the majority of the preparations studied hitherto have several types of receptors, such as guinea-pig ileum ($NK_1$, $NK_2$ and $NK_3$), some of them are said to possess only one type, such as dog carotid artery ($NK_1$), rabbit pulmonary artery devoid of endothelium ($NK_2$) and rat portal vein ($NK_3$) (D. REGOLI et al., Trends Pharmacol. Sci., 1988, 9, 290–295 and Pharmacology, 1989, 38, 1–15).

The recent synthesis of selective agonists has made it possible to characterize the various receptors more precisely. Thus [$Sar^9$, $Met-(O_2)^{11}$]SP, [$Nle^{10}$]$NKA_{4-10}$ and [$MePhe^7$]NKB are said to have a selectivity for the $NK_1$, $NK_2$ and $NE_3$ receptors respectively (q.v.D. REGOLI, 1988 and 1989, cited above).

It has now been found that certain aromatic amine compounds possess valuable pharmacological properties as neurokinin receptor antagonists and are especially useful for the treatment of any substance P-dependent and neurokinin-dependent pathological condition.

Thus, according to one of its features, the present invention relates to aromatic amine derivatives of the formula

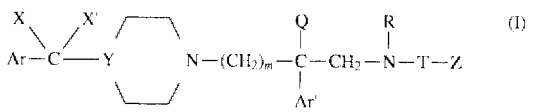

in which:

M is 2 or 3;

Ar and Ar' independently are a thienyl group; a phenyl group which is unsubstituted or mono- or di-substituted by a halogen atom, preferably a chlorine or fluorine atom, by a $C_1$–$C_3$ alkyl, by a trifluoromethyl, by an alkoxy in which the alkyl is $C_1$–$C_3$, by a hydroxyl or by a methylenedioxy; or an imidazolyl group; it also being possible for Ar' to be a benzothienyl group which is unsubstituted or substituted by a halogen, preferably by a chlorine or fluorine atom; a naphthyl group which is unsubstituted or substituted by a halogen, preferably by a fluorine atom; a biphenyl group; or an indolyl which is unsubstituted or substituted on the nitrogen by a benzyl group;

X is hydrogen;

X' is hydrogen or a hydroxyl group or is joined to X" below to form a carbon-carbon bond, or X and X' together form an oxo group or a dialkylaminoalkoxyimino group of the formula $=N-O-(CH_2)_p-Am$, in which p is 2 or 3 and Am is a dialkylamino group, it being possible for each alkyl to contain from 1 to 4 carbon atoms;

Y is a nitrogen atom or a group C(X"), in which X" is hydrogen or forms a carbon-carbon bond with X';

Q is hydrogen, a $C_1$–$C_4$ alkyl group or an aminoalkyl group of the formula $-(CH_2)_q-Am'$, in which q is 2 or 3 and Am' is a piperidino, 4-benzylpiperidino or dialkylamino group, it being possible for each alkyl to contain from 1 to 4 carbon atoms;

R is hydrogen, a methyl group or a group $(CH_2)_n-L$, in which n is an integer from 2 to 6 and L is hydrogen or an amino group;

T is a group selected from

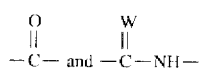

W being an oxygen or sulfur atom; and

Z is either hydrogen, or M or OM when T is the group $-C(=O)-$, or M when T is the group $-C(=W)-NH-$, M being hydrogen; a linear or branched $C_1$–$C_6$ alkyl; a phenylalkyl in which the alkyl group contains from 1 to 3 carbon atoms and which is unsubstituted or mono- or poly-substituted on the aromatic ring by a halogen, a hydroxyl, an alkoxy having 1 to 4 carbon atoms or an alkyl having 1 to 4 carbon atoms; a pyridylalkyl in which the alkyl group contains from 1 to 3 carbon atoms; a naphthylalkyl in which the alkyl group contains from 1 to 3 carbon atoms; a pyridylthioalkyl in which the alkyl group contains from 1 to 3 carbon atoms; a styryl; a 1-methylimidazol-2-yl-thioalkyl in which the alkyl group contains from 1 to 3 carbon atoms; a 1-oxophenyl-3-indan-2-yl; or an unsubstituted or mono- or poly-substituted aromatic or heteroaromatic group;

or to one of their salts with mineral or organic acids.

The salts of the compounds of formula (I) according to the present invention include those with mineral or organic acids which permit a suitable separation or crystallization of the compounds of formula (I), such as picric acid, oxalic acid or an optically active acid, for example a mandelic or camphosulfonic acid, as well as those which form pharmaceutically acceptable salts such as the hydrochloride, hydrobromide, sulfate, hydrogensulfate, dihydrogenphosphate, methanesulfonate, methylsulfate, maleate, fumarate, naphthalene-2-sulfonate, glycolate, gluconate, citrate and isethionate.

In particular, in formula (I), Z is a mono-, di- or tri-cyclic aromatic or heteroaromatic group which can carry one or more substituents and in which a carbon atom of the aromatic carbocycle or of the aromatic heterocycle is directly bonded to the group T.

More particularly, the radical Z can be a phenyl group which can be unsubstituted or may contain one or more substituents.

When Z is a phenyl group, this can preferably be mono- or di-substituted, especially in the 2,4-positions, but also for example in the 2,3-, 4,5-, 3,4 or 3,5-positions; it can also be trisubstituted, especially in the 2,4,6-positions, but also for example in the 2,3,4-, 2,3,5-, 2,4,5- or 3,4,5-positions, tetrasubstituted, for example in the 2,3,4,5-positions, or pentasubstituted. The substituents of the phenyl group can be: F; Cl; Br; I; CN; OH; $NH_2$; $NH-CO-NH_2$; $NO_2$; $CONH_2$; $CF_3$; $C_1-C_{10}$ alkyl, preferably $C_1-C_4$ alkyl, methyl or ethyl being preferred, as well as, for example, n-propyl, isopropyl, n-butyl, isobutyl, sec-butyl, tert-butyl, pentyl or n-pentyl, hexyl or n-hexyl, heptyl or n-heptyl, octyl or n-octyl, nonyl or n-nonyl or decyl or n-decyl; alkenyl containing 2 to 10 carbon atoms, preferably 2-4 carbon atoms, for example vinyl, allyl, prop-1-enyl, isopropenyl, butenyl or but-1-en-1-, -2-, -3- or -4-yl, but-2-en-1-yl, but-2-en-2-yl, pentenyl, hexenyl or decenyl; alkynyl containing 2 to 10 carbon atoms, preferably 2-4 carbon atoms, for example ethynyl, prop-1-yn-1-yl, propargyl, butynyl or but-2-yn-1-yl, pentynyl or decynyl; cycloalkyl containing 3 to 8 carbon atoms, preferably 5 or 6 carbon atoms, cyclopentyl or cyclohexyl being preferred, as well as, for example, cyclopropyl, cyclobutyl, 1-, 2- or 3-methylcyclopentyl, 1-, 2-, 3- or 4-methylcyclohexyl, cycloheptyl or cyclooctyl; bicycloalkyl containing 4 to 11 carbon atoms, preferably 7 carbon atoms, exo- or endo-2-norbornyl being preferred, as well as, for example, 2-isobornyl or 5-camphyl; hydroxyalkyl containing 1 to 5 carbon atoms, preferably 1–2 carbon atoms, hydroxymethyl and 1- or 2-hydroxyethyl being preferred, as well as, for example, 1-hydroxyprop-1-yl, 2-hydroxyprop-1-yl, 3-hydroxyprop-1-yl, 1-hydroxyprop-2-yl, 1-hydroxybut-1-yl or 1-hydroxypent-1-yl; hydroxypent-1-yl; alkoxy containing 1 to 10 carbon atoms, preferably 1–4 carbon atoms, methoxy or ethoxy being preferred, as well as, for example, n-propoxy, isopropoxy, n-butoxy, isobutoxy, sec-butoxy, tertbutoxy, pentoxy, hexyloxy, heptyloxy, octyloxy, nonyloxy or decyloxy; alkoxyalkyl containing 2 to 10 carbon atoms, preferably from 2 to 6 carbon atoms, for example alkoxymethyl or alkoxyethyl, such as methoxymethyl or 1- or 2-methoxyethyl, 1- or 2-n-butoxyethyl or 1- or 2-n-octyloxyethyl; alkoxyalkoxyalkyl containing up to 10 carbon atoms, preferably from 4 to 7 carbon atoms, for example alkoxyalkoxymethyl such as 2-methoxyethoxymethyl, 2-ethoxyethoxymethyl or 2-isopropoxyethoxymethyl, or alkoxyalkoxyethyl such as 2-(2-methoxyethoxy)ethyl or 2-(2-ethoxyethoxy)ethyl; alkoxyalkoxy containing from 2 to 10 carbon atoms, preferably from 3 to 6 carbon atoms, for example 2-methoxyethoxy, 2-ethoxyethoxy or 2-n-butoxyethoxy; alkenyloxy containing 2 to 10 carbon atoms, preferably 2 to 4 carbon atoms, allyloxy being preferred, as well as, for example, vinyloxy, propenyloxy, isopropenyloxy, butenyloxy such as but-1-en-1-, -2-, -3- or -4-yloxy, but-2-en-1-yloxy or but-2-en-2-yloxy, pentenyloxy, hexenyloxy or decenyloxy; alkenyloxyalkyl having up to 10 carbon atoms, preferably 3–6 carbon atoms, for example allyloxymethyl; alkynyloxy containing from 2 to 10 carbon atoms, preferably 2 to 4 carbon atoms, propargyloxy being preferred, as well as, for example, ethynyloxy, prop-1-yn-1-yloxy, butynyloxy or but-2-yn-1-yloxy, pentynyloxy or decynyloxy; alkynyloxyalkyl containing from 3 to 10 carbon atoms, preferably 3 to 6 carbon atoms, for example ethynyloxymethyl, propargyloxymethyl or 2-(but-2-yn-1-yloxy)ethyl; cycloalkoxy containing 3 to 8 carbon atoms, preferably 5 or 6 carbon atoms, cyclopentoxy or cyclohexyloxy being preferred, as well as, for example, cyclopropoxy, cyclobutoxy, 1-, 2- or 3-methylcyclopentoxy, 1-, 2-, 3- or 4-methylcyclohexyloxy, cycloheptyloxy or cyclooctyloxy; alkylthio containing from 1 to 10 carbon atoms, preferably 1 to 4 carbon atoms, methylthio or ethylthio being preferred, as well as, for example, n-propylthio, isopropylthio, n-butylthio, isobutylthio, sec-butylthio, tert-butylthio, pentylthio, hexylthio, octylthio, nonylthio or decylthio; alkylthioalkyl containing from 2 to 10 carbon atoms, preferably 2 to 6 carbon atoms, for example methylthiomethyl, 2-methylthioethyl or 2-n-butylthioethyl; acylamino, namely alkanoylamino containing from 1 to 7 carbon atoms, preferably 1 to 4 carbon atoms, formylamino and acetylamino being preferred, as well as propionylamino, butyrylamino, isobutyrylamino, valerylamino, caproylamino or heptanoylamino, or aroylamino or benzoylamino; acylaminoalkyl, preferably alkanoylaminoalkyl containing from 2 to 8 carbon atoms, preferably 3 to 6 carbon atoms, such as formylaminoethyl, acetylaminoethyl, propionylaminoethyl, n-butyrylaminoethyl, formylaminopropyl, acetylaminopropyl, propionylaminopropyl, formylaminobutyl or acetylaminobutyl, as well as propionylaminobutyl or butyrylaminobutyl; acyloxy containing from 1 to 6 carbon atoms, preferably 2 to 4 carbon atoms, acetyloxy, propionyloxy or butyryloxy being preferred, as well as, for example, formyloxy, valeryloxy or caproyloxy; alkoxycarbonyl containing from 2 to 5 carbon atoms, preferably 2 or 3 carbon atoms, methoxycarbonyl and ethoxycarbonyl being preferred, as well as, for example, n-propoxycarbonyl, isopropoxycarbonyl, n-butoxycarbonyl, isobutoxycarbonyl, sec-butoxycarbonyl or tert-butoxycarbonyl; cycloalkoxycarbonyl containing from 4 to 8 carbon atoms, preferably 6 or 7 carbon atoms, cyclopentoxycarbonyl and cyclohexyloxycarbonyl being preferred, as well as cyclopropoxycarbonyl, cyclobutoxycarbonyl or cycloheptyloxycarbonyl; alkylaminocarbonylamino containing from 2 to 4 carbon atoms, such as methylaminocarbonylamino, ethylaminocarbonylamino or propylaminocarbonylamino; dialkylaminocarbonylamino containing from 3 to 7 carbon atoms, preferably 3 to 5 carbon atoms, dimethylaminocarbonylamino being preferred, as well as di-n-propylaminocarbonylamino or diisopropylaminocarbonylamino; pyrrolidin-1-ylcarbonylamino; piperidin-1-ylcarbonylamino; cycloalkylaminocarbonylamino containing from 4 to 8 carbon atoms, preferably 6 or 7 carbon atoms, cyclopentylaminocarbonylamino and cyclohexylaminocarbonylamino being preferred, as well as cyclopropylaminocarbonylamino, cyclobutylaminocarbonylamino or cycloheptylaminocarbonylamino; alkylaminocarbonylaminoalkyl containing from 3 to 9 carbon atoms, preferably 4 to 7 carbon atoms, methylaminocarbonylaminoethyl, ethylaminocarbonylaminoethyl, ethylaminocarbonylaminopropyl and ethylaminocarbonylaminobutyl being preferred, as well as, for example, methylaminocarbonylaminomethyl, n-propylaminocarbonylaminobutyl and n-butylaminocarbonylaminobutyl; dialkylaminocarbonylaminoalkyl containing from 4 to 11 carbon atoms, for example dimethylaminocarbonylaminomethyl, diethylaminocarbonylaminoethyl, diethylaminocarbonylaminopropyl or diethylaminocarbonylaminobutyl; pyrrolidin-1-ylcarbonylaminoethyl; piperidin-1-ylcarbonylaminoethyl; cycloalkylaminocarbonylaminoalkyl containing from 5 to 12 carbon atoms, preferably 8 to 11 carbon atoms, cyclopentylaminocarbonylaminoethyl, cyclopentylaminocarbonylaminopropyl, cyclopentylaminocarbonylaminobutyl, cyclohexylaminocarbonylaminoethyl, cyclohexylaminocarbonylaminopropyl and cyclohexylaminocarbonylaminobutyl being preferred, as well as, for example, cyclopropylaminocarbonylaminomethyl or cycloheptylaminocarbonylaminoethyl; alkoxycarbonylaminoalkyl containing from 3 to 12 carbon atoms, preferably 4 to 9 carbon atoms, methoxycarbonylaminoethyl, ethoxycarbonylaminoethyl, n-propoxycarbonylaminoethyl, isopropoxycarbonylaminoethyl, n-butoxycarbonylaminoethyl, isobutoxycarbonylaminoethyl, sec-butoxycarbonylaminoethyl, tert-butoxycarbonylaminoethyl, ethoxycarbonylaminopropyl, n-butoxycarbonylaminopropyl, ethoxycarbonylaminobutyl and n-butoxycarbonylaminobutyl being preferred, as well as, for example, n-propoxycarbonylaminopropyl, n-propoxycarbonylaminobutyl or isopropoxycarbonylaminobutyl; cycloalkoxycarbonylaminoalkyl containing from 5 to 12 carbon atoms, preferably 8 to 11 carbon atoms, cyclopentoxycarbonylaminoethyl, cyclopentoxycarbonylaminopropyl, cyclopentoxycarbonylaminobutyl, cyclohexyloxycarbonylaminoethyl, cyclohexyloxycarbonylaminopropyl and cyclohexyloxycarbonylaminobutyl being preferred, as well as, for example, cyclopropoxycarbonylaminomethyl or cycloheptyloxycarbonylaminoethyl; carbamoylalkyl containing from 2 to 5 carbon atoms, preferably 2 carbon atoms, carbamoylmethyl being preferred, as well as carbamoylethyl, carbamoylpropyl or carbamoylbutyl; alkylaminocarbonylalkyl containing from 3 to 9 carbon atoms, preferably 3 to 6 carbon atoms, methylaminocarbonylethyl, ethylaminocarbonylmethyl, n-propylaminocarbonylmethyl, isopropylaminocarbonylmethyl, n-butylaminocarbonylmethyl, isobutylaminocarbonylmethyl, secbutylaminocarbonylmethyl and tert-butylaminocarbonylmethyl being preferred, as well as, for example, ethylaminocarbonylethyl, ethylaminocarbonylpropyl, ethylaminocarbonylbutyl, n-propylaminocarbonylbutyl or n-butylaminocarbonylbutyl; dialkylaminocarbonylalkyl containing from 4 to 11 carbon atoms, preferably 4 to 8 carbon atoms, dimethylaminocarbonylmethyl, diethylaminocarbonylmethyl, di-n-propylaminocarbonylmethyl, as well as, for example, diethylaminocarbonylethyl, diethylaminocarbonylpropyl, diethylaminocarbonylbutyl; pyrrolidin-1-ylcarbonylemthyl; piperidin-1-ylcarbonylmethyl; piperidin-1-yl carbonylethyl; cycloalkylaminocarbonylalkyl containing from 5 to 12 carbon atoms, preferably 7 or 8 carbon atoms, cyclopentylaminocarbonylmethyl and cyclohexylaminocarbonylmethyl being preferred, as well as, for example, cyclopropylaminocarbonylmethyl, cyclobutylaminocarbonylmethyl, cycloheptylaminocarbonylmethyl, cyclohexylaminocarbonylethyl, cyclohexylaminocarbonylpropyl or cyclohexylaminocarbonylbutyl; alkylaminocarbonylalkoxy containing from 3 to 10 carbon atoms, preferably 3 to 5 carbon atoms, methylaminocarbonylmethoxy being preferred, as well as, for example, methylaminocarbonylethoxy or methylaminocarbonylpropoxy; dialkylaminocarbonylalkoxy containing from 4 to 10 carbon atoms, preferably 4 to 7 carbon atoms, such as dimethylaminocarbonylmethoxy, diethylaminocarbonylethoxy or piperidin-1-ylcarbonylmethoxy; and cycloalkylaminocarbonylalkoxy containing from 5 to 11 carbon atoms, preferably 7 or 8 carbon atoms, such as cyclopentylaminocarbonylmethoxy or cyclohexylaminocarbonylmethoxy.

The group Z may advantageously be a phenyl group; a benzyl group; a benzoyl group; or a phenylthioalkyl group in which the alkyl is $C_1$–$C_3$.

The phenyl group Z is preferably mono- or di-substituted by a halogen, the 2,4-dichlorophenyl group being particularly preferred.

The radical Z can also be a bicyclic aromatic group such as naphth-1- or -2-yl or inden-1-, -2-, -3-, -4-, -5-, -6- or -7-yl, in which one or more bonds can be hydrogenated, it being possible for said groups to be unsubstituted or to contain one or more substituents such as: a halogen, and more particularly a fluorine atom, and alkyl, phenyl, cyano, hydroxyalkyl, hydroxyl, oxo, alkylcarbonylamino, alkoxycarbonyl and thioalkyl groups, in which the alkyls are $C_1$–$C_4$.

The radical Z can also be a pyridyl, thiadiazolyl, indolyl, indazolyl, imidazolyl, benzimidazolyl, quinolyl, benzotriazolyl, benzofuranyl, benzothienyl, benzothiazolyl, benzisothiazolyl, isoquinolyl, benzoxazolyl, benzisoxamolyl, benzoxazinyl, benzodioxinyl, isoxazolyl, benzopyranyl, thiazolyl, thienyl, furyl, pyranyl, chromenyl, isobenzofuranyl, pyrrolyl, pyrazolyl, pyrazinyl, pyrimidinyl, pyridazinyl, indolizinyl, phthalazinyl, quinazolinyl, acridinyl, isothiazolyl, isochromanyl or chromanyl group, in which one or more double bonds can be hydrogenated, it being possible for said groups to be unsubstituted or to contain one or more substituents such as: alkyl, phenyl, cyano, hydroxyalkyl, hydroxyl, alkylcarbonylamino, alkoxycarbonyl and thioalkyl groups, in which the alkyls are $C_1$–$C_4$.

According to another of its features, the present invention relates to a method of preparing variously substituted aromatic amino compounds of formula (I) and their salts, which comprises a) treating a free amine of the formula

in which m, Ar' and Q are as defined above; R° is hydrogen, a methyl group or a group $(CH_2)_n$—L°, in which n is as defined above and L° is hydrogen or an amino group protected by an N-protecting group; and E is a hydroxyl group, an O-protected group such as tetrahydropyran-2-yloxy, or a group

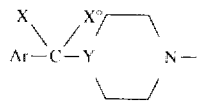

in which Ar, X and Y are as defined above and X° is the group X' as defined above, in which the hydroxyl group is protected by an O-protecting group, either with a functional derivative of an acid of the formula

in which Z is as defined above, when it is intended to prepare a compound of formula (I) in which T is —CO—, or with an iso(thio)cyanate of the formula

in which W and Z are as defined above, when it is intended to prepare a compound of formula (I) in which T is —C(W)—NH—, in order to form the compound of the formula

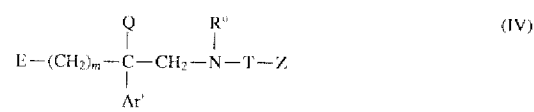

b) then, when E is tetrahydropyranyloxy, eliminating the tetrahydropyranyl group by acid hydrolysis, this hydrolysis being alternatively carried out in step a), on the starting amine of formula (II), c) treating the resulting N-substituted alkanolamine of the formula

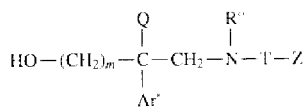  (V)

with methanesulfonyl chloride,

When the starting material used is a compound of formula (II) in which E is a group

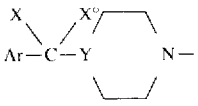

the method of the present invention can be represented and illustrated in detail by Scheme 1 below:

SCHEME 1

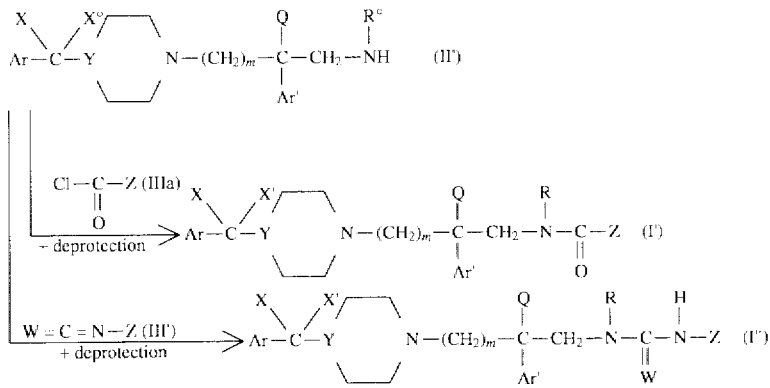

d) reacting the resulting mesylate of the formula

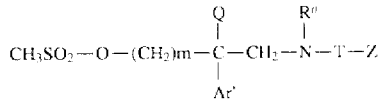  (VI)

with a secondary amine of the formula

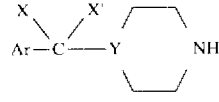  (VII)

in which Ar, Y, X and X' are as defined above, and e) eliminating any O-protecting and N-protecting groups present and, if appropriate, converting the resulting product into one of its salts.

The functional derivative of the acid (III) used is the acid itself, suitably activated for example by cyclohexylcarbodiimide or by benzotriazolyl-N-oxytrisdimethylaminophosphonium hexafluorophosphate (BOP), or one of the functional derivatives which react with amines, for example an anhydride, a mixed anhydride, the chloride or an activated ester. When Z is a group OM, the acid in question is carbonic acid and the functional derivative used is the monochloride, namely a chloroformate Cl—CO—OM.

Any N-protecting groups present in the group R° of the compound of formula (II) are the conventional N-protecting groups well known to those skilled in the art, and preferably those which can be eliminated by acid hydrolysis, such as the trityl and methoxytrityl groups.

Any O-protecting groups present in the group X° are also the conventional O-protecting groups well known to those skilled in the art, and preferably those which can be eliminated by mild acid hydrolysis, such as the tetrahydropyran-2-yl, t-butyldimethylsilyl and methoxymethyl groups.

In formula (IIIa) above, the acid chloride is considered to be a reactive functional derivative of the acid (III). The acid chloride is used when it is desired to prepare a compound (I') in which Z is OM. The reaction with the acid chloride is performed in an inert solvent such as methylene chloride or benzene, in the presence of a base such as, for example, triethylamine, at room temperature.

In the particular case where Z=OM, the reaction of the compound (II') with the chloroformate of the formula

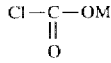

is performed by the usual methods.

When Z is other than OM, it is possible to use another functional derivative or to start from the free acid (III), carrying out a coupling reaction of (II') with BOP (benzotriazolyl-N-oxytrisdimethylaminophosphonium hexafluorophosphate) and then adding the acid (III) in the presence of an organic base such as, for example, triethylamine, in a solvent such as methylene chloride or dimethylformamide, at room temperature, the compounds (I') obtained being isolated and purified by the usual methods such as, for example, chromatography or recrystallization.

It is also possible to react (II') with an iso(thio)cyanate W=C=N—Z (III') in an anhydrous inert solvent such as, for example, benzene, overnight at room temperature, and then to treat the reaction mixture by the usual methods to give the compounds (I").

When the starting material used is a compound of formula (II) in which E is a tetrahydropyranyloxy group, the method of the present invention can be represented and illustrated by Scheme 2.

The reactions of the compound (II') with the reactants (IIIa) and (III') take place as described above for Scheme 1, it being possible for the acid chloride (IIIa) to be replaced with another functional derivative or with the free acid activated for example by BOP.

The resulting intermediate (IV') is deprotected by acid hydrolysis to give the free hydroxylated compound (V). Deprotection by hydrolysis of the tetrahydropyranyloxy group can be carried out direct on the compound (II"). This gives the hydroxylated compound (II'''), which is reacted direct with the reactant (IIIa) or (III'), as described in Scheme 2 below, to give the compound (V). This is followed by preparation of the mesylate (VI) and then substitution with a secondary amine of formula (VII), which finally gives the compounds (I) according to the invention after deprotection of the amine L° if appropriate.

Deprotection is carried out by the known methods; in particular, if a tetrahydropyranyl group is used as the O-protecting group, hydrolysis can be carried out under mild conditions with dilute p-toluenesulfonic acid. If the molecule of the product (IV) contains both a tetrahydropyranyloxy group and a tritylamino group, hydrolysis of the former can thus be carried out without affecting the N-protecting group, whereas formic acid removes both protecting groups at the same time.

The resulting products of formula (I) are isolated, in the form of the free base or a salt, by the conventional techniques.

When the compound of formula (I) is obtained in the form of the free base, salt formation is effected by treatment with

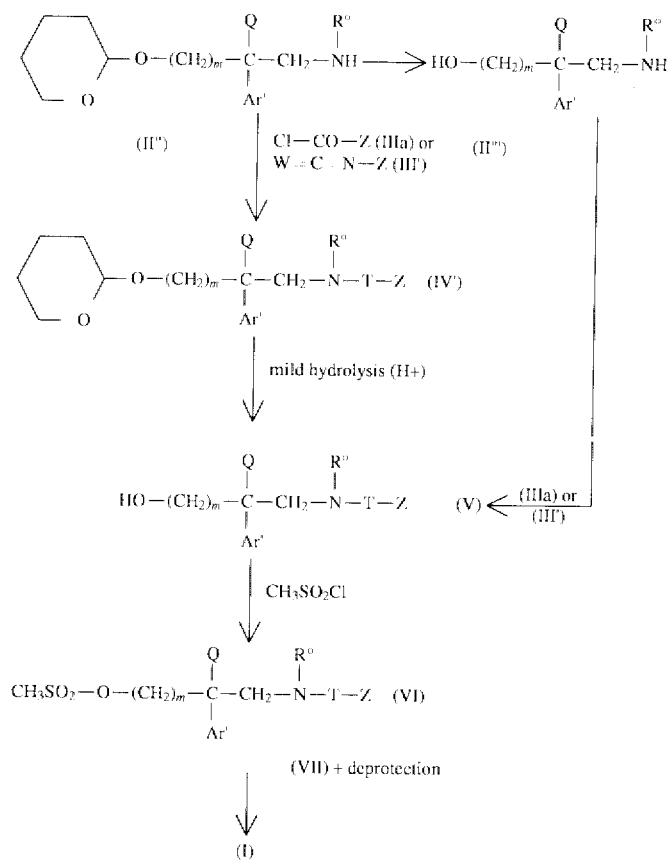

When the product obtained at the end of the reaction of the compound of formula (II) with the compound (III) (as a functional derivative) or (III') has formula (IV) in which E is a group

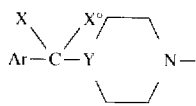

in which Ar, X, X° and Y are as defined above, the product can either be the final product or have an O-protected hydroxyl group (in X°) or a protected amino group.(L°) or both. In this last case, it is desirable to use the O-protecting and N-protecting groups in the starting material (II) so as to be able to hydrolyze them at the same time.

the chosen acid in an organic solvent. Treatment of the free base, for example dissolved in an alcohol such as isopropanol, with a solution of the chosen acid in the same solvent gives the corresponding salt, which is isolated by the conventional techniques. The hydrochloride, hydrobromide, sulfate, hydrogensulfate, dihydrogenphosphate, methanesulfonate, methylsulfate, oxalate, maleate, fumarate and naphthalene-2-sulfonate, for example, are prepared in this way.

When the reaction is complete, the compounds of formula (I) can be isolated in the form of one of their salts, for example the hydrochloride or the oxalate; in this case, where necessary, the free base can be prepared by neutralization of said salt with a mineral or organic base such as sodium hydroxide or triethylamine, or with an alkali metal carbonate or bicarbonate such as sodium or potassium carbonate or bicarbonate.

The enantiomers, which form part of the invention, can be isolated by resolution of the racemic mixtures (I).

It is also possible to resolve racemic mixtures of the products of formula (II), especially the products of formulae (II') and (II''') or precursors thereof, in order to prepare the enantiomers of the products of formula (I).

The starting compounds of formula (II) are prepared from nitriles of the formula $$E-(CH_2)_m-\underset{Ar'}{\underset{|}{C}}-CN \quad \text{(VIII)}$$

in which m, E, Q and Ar' are as defined above, by reduction and, if appropriate, alkylation of the amine obtained.

To prepare the compounds of formula (II) in which R° is hydrogen, the starting nitriles of formula (VIII) are hydrogenated in an alkanol such as ethanol, in the presence of a catalyst such as, for example, Raney nickel, and the free primary amine can be isolated by the conventional methods.

When it is desired to prepare the compounds of formula (II) in which R° is methyl, the free amine, obtained by hydrogenation of the nitrile (VIII) as described above, is treated with a chloroformate, for example with the chloroformate of the formula Cl—CO—OAlk, in which Alk is a $C_1$–$C_4$ alkyl, preferably ethyl, to give the carbamates of the formula $$E-(CH_2)_m-\underset{Ar'}{\underset{|}{C}}-CH_2-NH-\underset{O}{\underset{||}{C}}-OAlk$$

which are then reduced by known means such as reaction with a reducing agent like, for example, a metal hydride such as sodium aluminum hydride or lithium aluminum hydride, or a boron hydride such as borane dimethylsulfide. Reduction is carried out in a solvent such as ether or toluene, at a temperature between room temperature and 60° C. The resulting methylamine of the formula $$E-(CH_2)_m-\underset{Ar'}{\underset{|}{C}}-CH_2-\underset{|}{\overset{CH_3}{N}}-H \quad \text{(II, R° = CH_3)}$$

is isolated by the usual methods.

To prepare the compounds of formula (II) in which R° is a group —$(CH_2)_n$—L°, in which n and L° are as defined above, the free amine, obtained by hydrogenation of the nitrile (VIII) as described above, is treated with a reactive functional derivative of the acid of the formula $$L°-(CH_2)_{n-1}-COOH \quad \text{(IX)}$$

to give an amide of the formula $$E-(CH_2)_m-\underset{Ar'}{\underset{|}{C}}-CH_2-NH-CO-(CH_2)_{n-1}-L° \quad \text{(X)}$$

in which m, n, E, Ar', Q and L° are as defined above.

On reduction under the same conditions as those described above for the nitrile (VIII), the amide (X) gives the desired compound of the formula $$E-(CH_2)_m-\underset{Ar'}{\underset{|}{C}}-CH_2-NH-(CH_2)_n-L° \quad \text{(II, R° = (CH_2)_n-L°)}$$

The nitriles of formula (VIII) are prepared from known nitriles (commercially available or prepared by known methods) of the formula $$Ar'-\underset{|}{\overset{Q}{CH}}-CN \quad \text{(XI)}$$

which, on alkylation with a compound of the formula $$E-(CH_2)_m-J \quad \text{(XII)}$$

in which m and E are as defined above and J is a halogen atom, for example a bromine atom, or a hydroxyl group, give the desired compounds (VIII).

The nitriles of formula (VIII) in which E is a tetrahydropyranyloxy group are synthesized from a tetrahydropyranyloxy derivative (THP—O—) obtained by reacting an alkanol of the formula Br—$(CH_2)_m$—OH, where m is as defined above, with dihydropyran to give the compound $$Br-(CH_2)_m-O-\text{(THP)} \quad \text{(XII, E = THP—O—, J = Br)}$$

which is then added, in the presence of an alkali metal hydride, to the acetonitrile derivative (XI) in order to prepare the intermediate $$\text{(THP)}-O-(CH_2)_m-\underset{Ar'}{\underset{|}{C}}-CN \quad \text{(VIII, E = THP—O—, Q = H)}$$

corresponding to the compound of formula (VIII), which is an intermediate precursor of the compound (II') in Scheme 1 above in which Q is hydrogen, which can then be alkylated.

The nitriles of formula (VIII) in which E is a group $$\underset{Ar-C-Y}{\overset{X\diagdown\diagup X°}{\phantom{X}}}\phantom{-}N-$$

in which Ar, X, X° and Y are as defined above, are synthesized by known methods involving the addition of a nitrile derivative of the formula $$H-\underset{Ar'}{\underset{|}{\overset{Q}{C}}}-CN \quad \text{(XIV)}$$

to chlorinated derivatives of the formula $$\underset{Ar-C-Y}{\overset{X\diagdown\diagup X°}{\phantom{X}}}\phantom{-}N-(CH_2)_m-Cl \quad \text{(XIII)}$$

in the presence of sodium amide, in a solvent such as toluene, at temperatures of between 30° and 80° C.

The chlorinated derivative (XIII) is prepared by reacting a chlorinating reagent such as thionyl chloride, for example, with the hydroxylated derivative of the formula

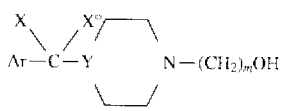
$$\text{(XV)}$$

which is itself prepared from the amine of the formula

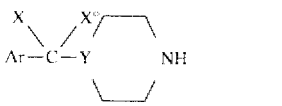
$$\text{(VII)}$$

by reaction with ethylene oxide if m=2 and a 3-halogenopropanol if m=3.

The amines (II) are novel products which form the key intermediates for the preparation of the compounds of formula (I) above. Moreover, it has been found, surprisingly, that like the compounds of formula (I), although to a lesser degree, the amines of formula (II) possess a good antagonistic activity towards neurokinin receptors. The activity of these compounds extends to the derivatives deprotected by the conventional methods referred to above ($X^\circ=X'$ and $R^\circ=R$).

Thus, according to another of its features, the present invention relates to compounds of the formula

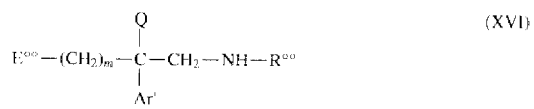
$$\text{(XVI)}$$

in which:

$E^{\circ\circ}$ is a tetrahydropyranyloxy group, a hydroxyl group, or a group

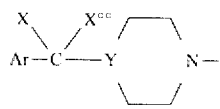

M is 2 or 3;

Ar and Ar' independently are a thienyl group; a phenyl group which is unsubstituted or mono- or di-substituted by a halogen atom, preferably a chlorine or fluorine atom, by a $C_1$–$C_3$ alkyl, by a trifluoromethyl, by an alkoxy in which the alkyl is $C_1$–$C_3$, by a hydroxyl or by a methylenedioxy; or an imidazolyl group; it being possible for Ar' to be a benzothienyl group which is unsubstituted or substituted by a halogen, preferably by a chlorine or fluorine atom; a naphthyl group which is unsubstituted or substituted by a halogen, preferably by a fluorine atom; a biphenyl group; or an indolyl which is unsubstituted or substituted on the nitrogen by a benzyl group;

X is hydrogen;

$X^{\circ\circ}$ is hydrogen or a hydroxyl group which is free or protected by an O-protecting group, or is joined to X" below to form a carbon-carbon bond, or X and $X^{\circ\circ}$ together form an oxo group or a dialkylaminoalkoxyimino group of the formula =N—O—$(CH_2)_p$—Am, in which p is 2 or 3 and Am is a dialkylamino group, it being possible for each alkyl to contain from 1 to 4 carbon atoms;

Y is a nitrogen atom or a group C(X"), in which X" is hydrogen or forms a carbon-carbon bond with $X^{\circ\circ}$;

Q is hydrogen, a $C_1$–$C_4$ alkyl group or an aminoalkyl group of the formula —$(CH_2)_q$—Am', in which q is 2 or 3 and Am' is a piperidino, 4-benzylpiperidino or dialkylamino group, it being possible for each alkyl to contain from 1 to 4 carbon atoms; and $R^{\circ\circ}$ is hydrogen, a methyl group or a group $(CH_2)_n$—$L^{\circ\circ}$, in which n is a number from 2 to 6 and $L^{\circ\circ}$ is hydrogen or an amino group which is free or protected by an N-protecting group;

or to one of their salts.

The compounds of formula (XVI) include the compounds of formula (II) which are protected compounds, as well as the corresponding deprotected compounds.

The compounds of formula XVI, provided that when m=2, $E^{\circ\circ}$ is a hydroxyl group, $R^{\circ\circ}$ is hydrogen and Ar' is an unsubstituted phenyl, then Q is different from H, ethyl, or propyl when m=2, $E^{\circ\circ}$ is a hydroxyl group, $R^{\circ\circ}$ is hydrogen and Q is hydrogen, then Ar' is different from a 3,4-dimethoxyphenyl group or a 2-thienyl group when m=3, $E^{\circ\circ}$ is a hydroxyl group, Ar' is an unsubstituted phenyl, Q is ethyl, then $R^{\circ\circ}$ is not hydrogen are novel products.

They are obtained by the process described above for the obtention of compounds of formula (II), in which each step may be eventually followed by the elimination of N- and O-protecting groups. They may then be transformed into salts with optically active acids, which allows the preparation of optically pure compounds.

The compounds of formula (XVI) which are particularly preferred are those in which $E^{\circ\circ}$ is a hydroxyl group and $R^{\circ\circ}$ is hydrogen; these compounds and their enantiomers are the compounds of formula (II''').

The intermediates of formula (IV) in which E is tetrahydropyranyloxy and the intermediates of formula (V) and of formula (VI) are particularly advantageous novel products and represent a further feature of the present invention. These products, and the corresponding compounds from which the O- and N-protecting groups have been removed by conventional methods, can be jointly represented by formula (V') below:

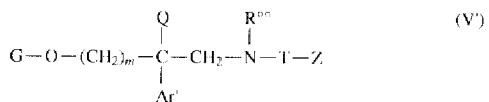
$$\text{(V')}$$

in which:

m is 2 or 3;

G is hydrogen, a tetrahydropyranyl group or a methanesulfonyl group;

Ar' is a thienyl group; a phenyl group which is unsubstituted or mono- or di-substituted by a halogen atom, preferably a chlorine or fluorine atom, by a trifluoromethyl group, by an alkoxy in which the alkyl is $C_1$–$C_3$ or by a hydroxyl; a benzothienyl group which is unsubstituted or substituted by a halogen; a naphthyl group which is unsubstituted or substituted by a halogen, preferably a fluorine atom; a biphenyl group; or an indolyl group which is unsubstituted or substituted on the nitrogen by a benzyl;

Q is hydrogen or an aminoalkyl group of the formula —$(CH_2)_q$—Am', in which q is 2 or 3 and Am' is a piperidino, 4-benzylpiperidino or dialkylamino group, it being possible for each alkyl to contain from 1 to 4 carbon atoms;

$R^{\circ\circ}$ is hydrogen a methyl group or a group $(CH_2)_n$—$L^{\circ\circ}$, in which n is an integer from 2 to 6 and $L^{\circ\circ}$ is hydrogen or an amino group which is free or protected by an N-protecting group;

T is a group selected from

W being an oxygen or sulfur atom; and

Z is either hydrogen, or M or OM when T is the group —C(=O)—, or M when T is the group —C(=W)—NH—, M being hydrogen; a linear or branched $C_1$–$C_6$ alkyl; a phenylalkyl in which the alkyl group contains from 1 to 3 carbon atoms and which is unsubstituted or mono- or poly-substituted on the aromatic ring by a halogen, a hydroxyl, an alkoxy having 1 to 4 carbon atoms or an alkyl having 1 to 4 carbon atoms; a pyridylalkyl in which the alkyl group contains from 1 to 3 carbon atoms; a naphthylalkyl in which the alkyl group contains from 1 to 3 carbon atoms; a pyridylthioalkyl in which the alkyl group contains from 1 to 3 carbon atoms; a styryl; a 1-methylimidazol-2-ylthioalkyl in which the alkyl group contains from 1 to 3 carbon atoms; a 1-oxophenyl-3-indan-2-yl; or an unsubstituted or mono- or poly-substituted aromatic or heteroaromatic group;

and their salts with mineral or organic acids.

The compounds of formula (V') provided that when m=3, G is hydrogen, Ar' is an unsubstituted phenyl group, Q is an ethyl group, T is

and Z is a methyl group, then R°° is different from hydrogen, are novel products. These compounds are prepared according to Steps a), b) and c) of the method described above for the preparation of the compounds of formula (I), which are eventually followed by the elimination of N-protecting groups after each step, except that a free amine of the formula

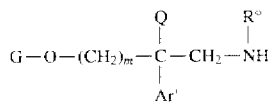

in which m, G, Q, Ar' are as defined above and R° is hydrogen, a methyl group, a group $(CH_2)_n$—L° in which n is an integer from 2 to 6 and L° is hydrogen or an amino group protected by an N-protecting group, is used as the starting material.

As indicated above, the intermediates which are capable of giving salts with optically active acids can be resolved so as to make it possible to prepare the enantiomers of the compounds of formula (I).

It is also possible to make provision for the stereospecific synthesis of intermediates which do not give a salt permitting separation.

A particularly suitable intermediate for such a stereospecific synthesis is the alcohol of formula (V) above.

Thus, according to another of its features, the present invention relates to the enantiomers and to a method of preparing the enantiomers of the compounds of formula (I) and their salts; said enantiomers have formula (I*) below:

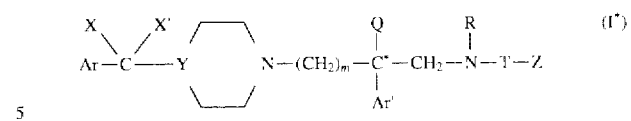

in which:

Ar, Ar', Z, X, X', Y, Q, R, T and m are as defined above and "*" means that the carbon atom denoted by this symbol has a defined (+) or (−) absolute configuration.

This method comprises treating a compound of the formula

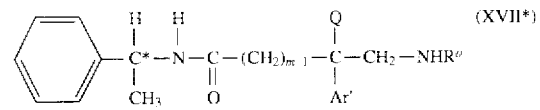

in a solvent such as, for example, dioxane, in an acid medium, for example in the presence of hydrochloric acid, to give the amino acid of the formula

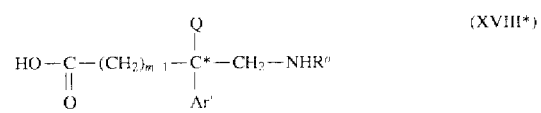

which is esterified in an alkanol AlkOH, in which Alk is an alkyl having 1 to 4 carbon atoms, in an acid medium, and then treating the corresponding ester of the formula

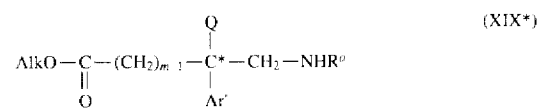

in which Alk, Q, Ar', R° and m are as defined above, either with a functional derivative of an acid of the formula

or with an iso(thio)cyanate of the formula

Z and W being as defined above, under operating conditions identical to those used for the preparation of the derivatives (IV) above, to give the ester of the formula

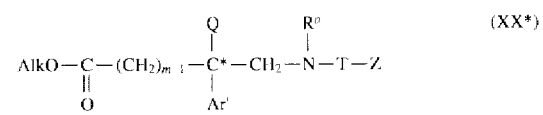

which is then reduced to the corresponding alcohol of the formula

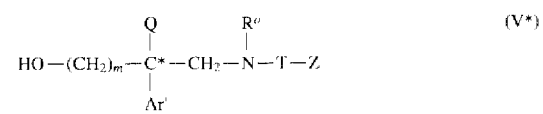

These alcohols (V*) correspond to the compounds of formula (V') above in which m, Q, T, Ar' and Z are as defined above, G is hydrogen and R°° is R°, the latter being as defined above, said compounds being in optically pure form. These compounds are novel and form part of the invention.

The alcohol (V*) is converted into the methanesulfonate derivative of the formula

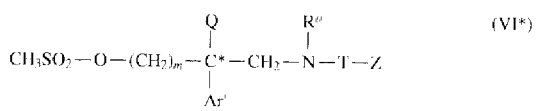

under operating conditions identical to those used for the preparation of the derivatives (VI) above.

The derivatives (VI*) correspond to the compounds of formula (V') above in which m, Q, T, Ar' and Z are as defined above, G is methanesulfonyl and R°° is R°, the latter being as defined above, said compounds being in optically pure form. These compounds are novel and form part of the invention.

Substitution of the mesylate (VI*) with an amine of the formula

under the conditions described for the preparation of (I) above makes it possible to prepare the derivatives (I*), after deprotection if appropriate, these derivatives being eventually transformed into one of their salts, using known methods.

The compounds of formula (XVII*) are known or can easily be prepared by the method described by G. HELMCHEN et al., Angew. Chem. Int. Ed. Engl., 1979, 1, 18, 65, according to the following scheme:

SCHEME 3

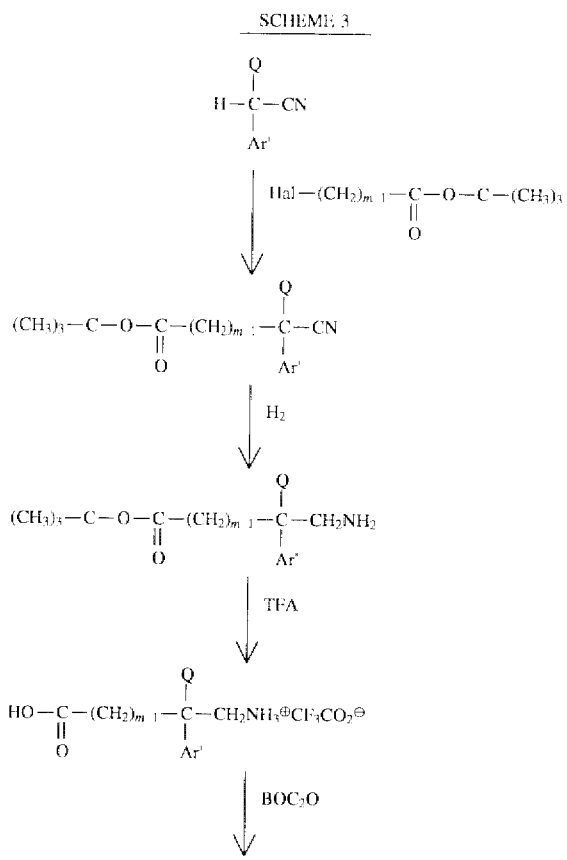

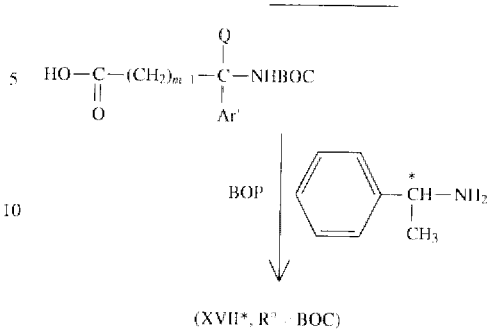

(XVII*, R° = BOC)

The resulting products of formula (I*) are isolated, in the form of the free base or a salt, by the conventional techniques.

When the compound of formula (I*) is obtained in the form of the free base, salt formation is effected by treatment with the chosen acid in an organic solvent. Treatment of the free base, for example dissolved in an alcohol such as isopropanol, with a solution of the chosen acid in the same solvent gives the corresponding salt, which is isolated by the conventional techniques. The hydrochloride, hydrobromide, sulfate, hydrogensulfate, dihydrogenphosphate, methanesulfonate, methylsulfate, oxalate, maleate, fumarate and naphthalene-2-sulfonate, for example, are prepared in this way.

When the reaction is complete, the compounds of formula (I*) can be isolated in the form of one of their salts, for example the hydrochloride or the oxalate; in this case, where necessary, the free base can be prepared by neutralization of said salt with a mineral or organic base.

The compounds according to the invention were subjected to biochemical and pharmacological tests.

The compounds (I) and (I*) and the compounds (XVI) in which

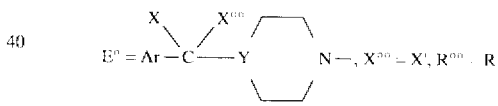

and their salts showed antagonistic properties towards the binding of substance P in tests performed on rat cortical membranes and IM9 lymphoblast membranes, according to M. A. CASCIERI et al., J. Biol. Chem., 1983, 258, 5158–5164 and D. D. PAYA etal., J. Immunol., 1984, 133, 3260–3265.

The same compounds and their salts showed antagonistic properties towards the binding of NKA in tests performed on rat duodenal membranes, according to L. BERGSTOM etal., Mol. Pharmacol., 1987, 32, 764–771.

The same compounds and their salts showed antagonistic properties towards specific $NK_1$, $NK_2$ and $NK_3$ receptor agonists in tests performed on different isolated organs, according to D. REGOLI et al., Trends Pharmacol. Sci., 1988, 9, 290–295.

The same compounds and their salts showed overall antagonistic properties towards $NK_1$, $NK_2$ and $NK_3$ in tests performed on different isolated organs, according to D. REGOLI etal., Trends Pharmacol. Sci., 1988, 9, 290–295 and Pharmacology, 1989, 38, 1–15.

The same compounds and their salts showed antagonistic properties towards the hypermotility induced in rats by substance P in pharmacological tests performed according to Elliot et al., Brain Res., 1986, 381, 68–76.

The antagonistic properties towards the salivation induced in rats by substance P or a specific $NK_1$ agonist ([$Sar^9Met(O2)^{11}$]SP) were demonstrated by means of pharmacological tests performed according to TAKEDA Y. and KRAUSE J. E., Proc. Natl. Acad. Sci. USA, 1989, 86, 392–396.

The analgesic properties were demonstrated by means of pharmacological tests performed on arthritic rats according to V. KAYSER et al., Proceedings of the Vth World Congress on Pain, DUMMER R., GEBHART G. F. and BOND M. R. ed., Elsevier Biomedical Division, 1988, 72–79.

The compounds of the present invention have a low toxicity; in particular, their acute toxicity is compatible with their use as drugs. For such a use, an effective amount of a compound of formula (I), (I*) or (XVI) or of one of their pharmaceutically acceptable salts is administered to mammals.

The compounds of the present invention are generally administered in dosage units. Said dosage units are preferably formulated as pharmaceutical compositions in which the active principle is mixed with a pharmaceutical excipient.

Thus, according to another of its features, the present invention relates to pharmaceutical compositions containing, as the active principle, a compound of formula (I) or (I*) or of formula (XVI) or one of their pharmaceutically acceptable salts.

The compounds of formula (I), (I*) or (XVI) above and their pharmaceutically acceptable salts can be used at daily doses of 0.01 to 100 mg per kilo of body weight of the mammal to be treated, preferably at daily doses of 0.1 to 50 mg/kg. In humans, the dose can preferably vary from 0.5 to 4000 mg per day, more particularly from 2.5 to 1000 mg, depending on the age of the subject to be treated or the type of treatment: prophylactic or curative.

In the pharmaceutical compositions of the present invention for oral, sublingual, subcutaneous, intramuscular, intravenous, percutaneous, local or rectal administration, the active principles can be administered in unit forms of administration, mixed with conventional pharmaceutical carriers, to animals and to humans. The appropriate unit forms of administration include oral forms such as tablets, gelatin capsules, powders, granules and solutions or suspensions to be taken orally, sublingual and buccal forms of administration, subcutaneous, intramuscular, intravenous, intranasal or intraocular forms of administration and rectal forms of administration.

When a solid composition is prepared in the form of tablets, the main active principle is mixed with a pharmaceutical vehicle such as gelatin, starch, lactose, magnesium stearate, talc, gum arabic or the like. The tablets can be coated with sucrose or other appropriate substances or they can be treated so as to have a prolonged or delayed activity and so as to release a predetermined amount of active principle continuously.

A preparation in the form of gelatin capsules is obtained by mixing the active principle with a diluent and pouring the mixture obtained into soft or hard gelatin capsules.

A preparation in the form of a syrup or elixir can contain the active principle together with a sweetener, which is preferably calorie-free, methylparaben and propylparaben as antiseptics, a taste corrector and an appropriate colorant.

The water-dispersible granules or powders can contain the active principle mixed with dispersants or wetting agents, or suspending agents such as polyvinylpyrrolidone, as well as with sweeteners or taste correctors.

For rectal administration, suppositories are used which are prepared with binders melting at the rectal temperature, for example cacao butter or polyethylene glycols.

For parenteral, intranasal or intraocular administration, aqueous solutions, isotonic saline solutions or sterile injectable solutions are used which contain pharmacologically compatible dispersants and/or wetting agents, for example propylene glycol or butylene glycol.

The active principle can also be formulated as microcapsules, with one or more carriers or additives if appropriate.

The following Examples illustrate the invention without however implying a limitation.

EXAMPLE 1

N-[4-(4-Benzylpiperidin-1-yl)-2-(3,4-dichlorophenyl)butyl]-2,4-dichlorobenzamide hydrochloride. SR 45672 A (I):

m = 2; Q = H;

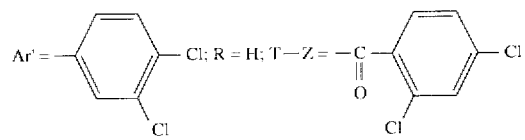

A) 1-Amino-4-(4-benzylpiperidin-1-yl)-2-(3,4-dichlorophenyl)butane dihydrochloride 14.5 g of 4-(4-benzylpiperidin-1-yl)-2-(3,4-dichlorophenyl)butyronitrile hydrochloride are dissolved in 400 ml of 95° ethanol. A solution of 20 ml of concentrated ammonia in 40 ml of water and Raney nickel (10% by weight of the amount of amine) are added to the mixture, which is then placed under a hydrogen atmosphere, with vigorous stirring, for 4 hours, after which 1.67 l of hydrogen have been consumed. After filtration of the catalyst, the filtrate is concentrated under vacuum and the residue is taken up in ethyl acetate, washed with water, dried and concentrated under vacuum. The residue is taken up in a solution of hydrogen chloride in methanol, filtered off and recrystallized from a 3/7 acetone/ether mixture.

m=10.2 g

M.p.=210° C.

B) SR 45672 A 2.3 g of the product obtained above and 1 g of 2,4-dichlorobenzoyl chloride are dissolved in 100 ml of methylene chloride in the presence of 0.03 g of triethylamine. The reaction mixture is stirred for 4 hours at room temperature and then concentrated under vacuum and the residue is taken up in water, extracted with ether, dried over $MgSO_4$ and concentrated under vacuum. The residue is chromatographed on silica gel using a 97/3 methylene chloride/methanol mixture as the eluent. Concentration of the pure fractions gives a residue, which is taken up in a solution of hydrogen chloride in ether.

m=1 g

M.p.=86°–87° C.

EXAMPLE 2

N-[5-(4-Benzylpiperidin-1-yl)-2-(3,4-dichlorophenyl)pentyl]-2,4-dichlorobenzamide hydrochloride. SR 45083 A (I):

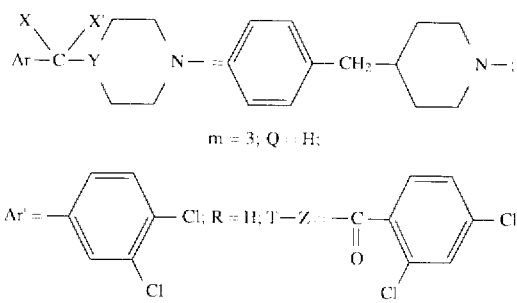

m = 3; Q = H;

Ar' = [2,4-dichlorophenyl]; R = H; T—Z = —C(=O)—[2,4-dichlorophenyl]

If the procedure of Example 1 is followed, except that 5-(4-benzylpiperidin-1-yl)-2-(3,4-dichlorophenyl)pentylnitrile is used as the starting material, SR 45083 A is obtained, which is recrystallized from a methylene chloride/pentane mixture.

M.p. = 98°–100° C.

EXAMPLE 3

N-[4-(4-Benzylpiperidin-1-yl)-2-(3,4-difluorophenyl)butyl]-2,4-dimethylbenzamide hydrochloride hemihydrate. SR 46316 A (I):

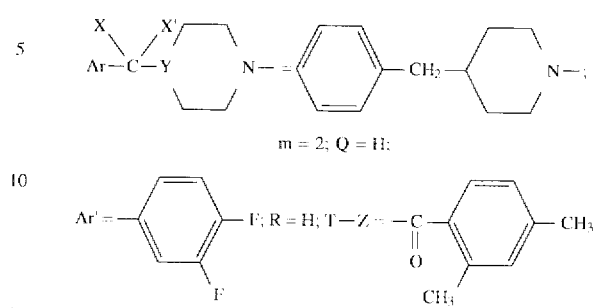

m = 2; Q = H;

Ar' = [3,4-difluorophenyl]; R = H; T—Z = —C(=O)—[2,4-dimethylphenyl]

1.2 g of BOP are added to a solution of 1 g of 1-amino-3-(4-benzylpiperidin-1-yl)-2-(3,4-difluorophenyl)butane, 0.34 g of 2,4-dimethylbenzoic acid and 1 g of triethylamine in 50 ml of methylene chloride. The reaction mixture is stirred for one hour at room temperature and concentrated under vacuum. The residue is taken up in water, extracted with ether, washed with water and then with a solution of sodium bicarbonate, dried over $MgSO_4$ and then concentrated under vacuum. The residue is taken up in methylene chloride for preparation of the hydrochloride, which is filtered off and washed with ether.

m=0.4 g

M.p.=99°–103° C.

The compounds described in Tables 1 and 2 were prepared according to Example 1, 2 or 3.

In the formula below, the group Z indicated in formula I is a phenyl group which is unsubstituted or mono-, di- or tri-substituted by A, A' and A".

TABLE 1

| Product SR (Example n°) | Ar' | A | A' | A" | M.p., °C. Recryst. solvent. Salt |
|---|---|---|---|---|---|
| 47807 A (4) | phenyl | H | H | H | 116 isopropyl ether HCl |
| 46679 A (5) | 3,4-dichlorophenyl | 2-F | H | H | 100–102 pentane/ether HCl.0.5 H₂O |
| 46101 A (6) | 4-fluorophenyl | 2-F | 4-F | H | 81–84 CH₂Cl₂/ether HCl.0.5 H₂O |

TABLE 1-continued
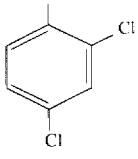
| Product SR (Example n°) | Ar' | A | A' | A" | M.p., °C. Recryst. solvent. Salt |
|---|---|---|---|---|---|
| 46099 A (7) | 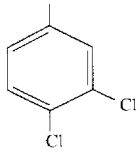 2,4-diCl | 2-F | 4-F | H | 78–80 CH₂Cl₂/ether HCl.0.5 H₂O |
| 45966 A (8) | 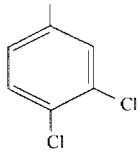 3,4-diCl | 2-F | 4-F | H | 83–86 isopropyl ether HCl.0.5 H₂O |
| 46032 A (9) | 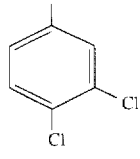 3,4-diCl | 2-Cl | H | H | 186 ether HCl |
| 47704 A (10) | 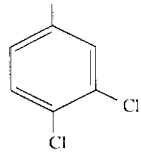 3,4-diCl | 3-Cl | H | H | 158–160 AcOEt HCl |
| 46454 A (11) | 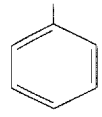 3,4-diCl | 4-Cl | H | H | 112–114 CH₂Cl₂/ether HCl.0.5 H₂O |
| 47462 A (12) | 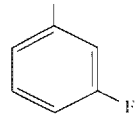 phenyl | 2-Cl | 4-Cl | H | 95 ether HCl.0.5 H₂O |
| 47801 A (13) | 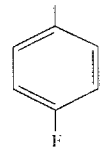 3-F | 2-Cl | 4-Cl | H | 108 ether HCl.0.5 H₂O |
| 46100 A (14) | 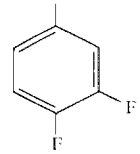 4-F | 2-Cl | 4-Cl | H | 95–97 CH₂Cl₂/ether HCl.0.5 H₂O |
| 46238 A (15) | 3,4-diF | 2-Cl | 4-Cl | H | 96–101 isopropyl ether HCl.0.5 H₂O |

TABLE 1-continued

Structure: Ph-CH₂-[piperidine]-N-CH₂-CH₂-CH(Ar')-CH₂-NH-C(=O)-[phenyl with A, A', A"]

| Product SR (Example n°) | Ar' | A | A' | A" | M.p., °C. Recryst. solvent. Salt |
|---|---|---|---|---|---|
| 45910 A (16) | 3-Cl-phenyl | 2-Cl | 4-Cl | H | 83–85<br>CH₂Cl₂/ether<br>HCl |
| 46152 A (17) | 4-Cl-phenyl | 2-Cl | 4-Cl | H | 94<br>pentane/ether<br>HCl·0.5 H₂O |
| 46011 A (18) | 2,4-diCl-phenyl | 2-Cl | 4-Cl | H | 107–110<br>ether<br>HCl |
| 45672 B (19a) | 3,4-diCl-phenyl | 2-Cl | 4-Cl | H | 88–90<br>pentane<br>methanesulfonate hydrate |
| 45672 C (19b) | 3,4-diCl-phenyl | 2-Cl | 4-Cl | H | 70–72<br>pentane<br>glycolate |
| 45672 D (19c) | 3,4-diCl-phenyl | 2-Cl | 4-Cl | H | 144–146<br>pentane<br>gluconate |
| 45672 E (19d) | 3,4-diCl-phenyl | 2-Cl | 4-Cl | H | 103–105<br>pentane<br>citrate<br>hemihydrate |
| 45672 F (19e) | 3,4-diCl-phenyl | 2-Cl | 4-Cl | H | 86–90<br>pentane<br>isethionate<br>hemihydrate |

TABLE 1-continued
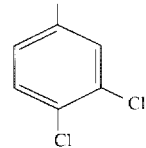
| Product SR (Example n°) | Ar' | A | A' | A" | M.p., °C. Recryst. solvent. Salt |
|---|---|---|---|---|---|
| 45672 H (19) | 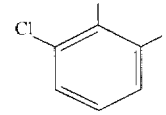 | 2-Cl | 4-Cl | H | 136–138 methanol free base |
| 46153 A (20) | 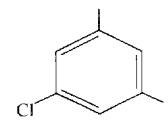 | 2-Cl | 4-Cl | H | 104–106 pentane/ether HCl |
| 46183 A (21) | 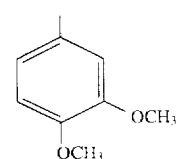 | 2-Cl | 4-Cl | H | 117–121 ether HCl |
| 46364 A (22) | 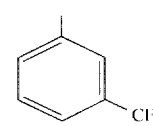 | 2-Cl | 4-Cl | H | 92 $CH_2Cl_2$/ether HCl.0.5 $H_2O$ |
| 47158 A (23) | 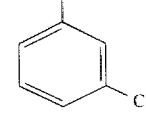 | 2-Cl | 4-Cl | H | 96–98 pentane/ether HCl |
| 47225 A (24) | 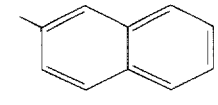 | 2-Cl | 4-Cl | H | 92 pentane/ether HCl |
| 46498 A (25) | 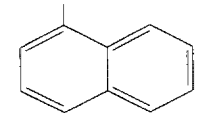 | 2-Cl | 4-Cl | H | 112–114 $CH_2Cl_2$/ether HCl.0.5 $H_2O$ |
| 45261 A (26) | 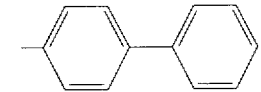 | 2-Cl | 4-Cl | H | 90–94 isopropanol methanesulfonate |
| 45870 A (27) |  | 2-Cl | 4-Cl | H | 112–114 pentane HCl.0.5 $H_2O$ |
| 46362 A (28) |  | 2-Cl | 4-Cl | H | 102 pentane HCl |

TABLE 1-continued

Structure: Benzyl-piperidine-N—CH$_2$—CH$_2$—CH(Ar')—CH$_2$—NH—C(=O)—C$_6$H$_2$(A)(A')(A'')

| Product SR (Example n°) | Ar' | A | A' | A'' | M.p., °C. Recryst. solvent. Salt |
|---|---|---|---|---|---|
| 47743 A (29) | indol-3-yl (NH) | 2-Cl | 4-Cl | H | 115–118 AcOEt HCl |
| 46844 A (30) | 1-benzyl-indol-3-yl | 2-Cl | 4-Cl | H | 126–128 ether HCl.0.5 H$_2$O |
| 46360 A (31) | benzo[b]thiophen-3-yl | 2-Cl | 4-Cl | H | 138–144 CH$_2$Cl$_2$/ether HCl |
| 46206 A (32) | 4-Cl-C$_6$H$_4$ | 3-Cl | 5-Cl | H | 108 CH$_2$Cl$_2$/ether 108 |
| 46236 A (33) | 2,6-diCl-C$_6$H$_3$ | 3-Cl | 5-Cl | H | 90 CH$_2$Cl$_2$/ether HCl |
| 46501 A (34) | 3,4-diCl-C$_6$H$_3$ | 2-Cl | 6-Cl | H | 128–130 CH$_2$Cl$_2$/ether HCl.0.5 H$_2$O |
| 46499 A (35) | 3,4-diCl-C$_6$H$_3$ | 2-Cl | 4-I | H | 112–114 CH$_2$Cl$_2$/ether HCl.0.5 H$_2$O |
| 45871 A (36) | naphth-1-yl | 2-Cl | 4-OH | H | 142–144 CH$_2$Cl$_2$/ether HCl.0.5 H$_2$O |
| 46815 A (37) | 3,4-diCl-C$_6$H$_3$ | 2-Cl | 4-CH$_3$ | H | 92 hexane HCl |

TABLE 1-continued

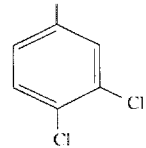

| Product SR (Example n°) | Ar' | A | A' | A" | M.p., °C, Recryst. solvent, Salt |
|---|---|---|---|---|---|
| 47146 A (38) | 3,4-diCl-phenyl | 2-Cl | 4-NO₂ | H | 160–164 AcOEt HCl |
| 46221 A (39) | 3,4-diCl-phenyl | 4-OH | H | H | 134 ether HCl |
| 46315 A (40) | 3,4-diF-phenyl | 2-OH | 4-OH | H | 136–141 CH₂Cl₂/ether HCl.0.5 H₂O |
| 45911 A (41) | 3-Cl-phenyl | 3-CF₃ | H | H | 86–89 ether HCl.0.5 H₂O |
| 46561 A (42) | 3,4-diCl-phenyl | 2-OCH₃ | 4-OCH₃ | H | 104 CH₂Cl₂/ether HCl |
| 45912 A (43) | 3-Cl-phenyl | 3-OCH₃ | 4-OCH₃ | H | 86–89 ether HCl.0.5 H₂O |
| 47800 A (44) | 3,4-diCl-phenyl | 3-NO₂ | 4-F | H | 119 AcOEt HCl |
| 46828 A (45) | 3,4-diCl-phenyl | 2-NO₂ | 4-NO₂ | H | 112–120 isopropyl ether HCl |
| 46758 A (46) | 3,4-diCl-phenyl | 3-NO₂ | 5-NO₂ | H | 194–198 ether HCl |

TABLE 1-continued

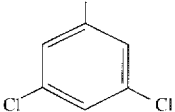

| Product SR (Example n°) | Ar' | A | A' | A" | M.p., °C. Recryst. solvent. Salt |
|---|---|---|---|---|---|
| 46184 A (47) | 3,5-diCl-phenyl | 3-NO₂ | 5-NO₂ | H | 115–120 ether HCl |
| 46526 A (48) | 3,4-diCl-phenyl | 2-CH₃ | 4-CH₃ | 6-CH₃ | 128–130 CH₂Cl₂/ether HCl |
| 46888 A (49) | 3,4-diCl-phenyl | 2-phenyl | H | H | 175 ether HCl |
| 46209 A (50) | 3,4-diCl-phenyl | 4-phenyl | H | H | 195 ether HCl |
| 46560 A (51) | 3,4-diCl-phenyl | 2-C(O)-phenyl | H | H | 132 CH₂Cl₂/ether HCl |
| 46317 A (52) | 3,4-diF-phenyl | 4-C(O)-phenyl | H | H | 95–100 CH₂Cl₂/ether HCl·0.5 H₂O |
| 46672 A (53) | 3,4-diCl-phenyl | 4-CH₂-S-phenyl | H | H | 134 ether HCl |
| 46391 A (54) | 3,4-diCl-phenyl | 4-CH₂-S-(1-methylimidazol-2-yl) | H | H | 207 ethyl acetate 2HCl |

TABLE 1-continued
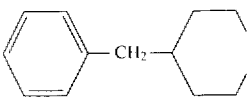
| Product SR (Example n°) | Ar' | A | A' | A" | M.p., °C. Recryst. solvent. Salt |
|---|---|---|---|---|---|
| 46209 A (50) | 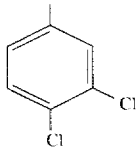 3,4-diCl | 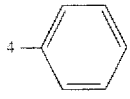 4- | H | H | 195 ether HCl |
| 46560 A (51) | 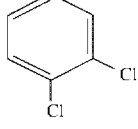 3,4-diCl | 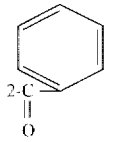 2-C(=O)- | H | H | 132 CH$_2$Cl$_2$/ether HCl |
| 46317 A (52) | 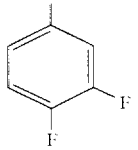 3,4-diF | 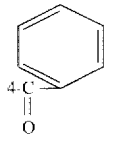 4-C(=O)- | H | H | 95–100 CH$_2$Cl$_2$/ether HCl 0.5 H$_2$O |
| 46672 A (53) | 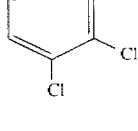 3,4-diCl | 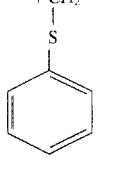 4-CH$_2$-S-Ph | H | H | 134 ether HCl |
| 46391 A (54) | 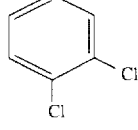 3,4-diCl | 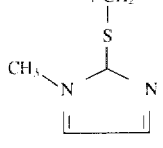 4-CH$_2$-S-(1-methylimidazol-2-yl) | H | H | 207 ethyl acetate 2HCl |
| 46390 A (55) | 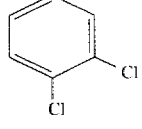 3,4-diCl | 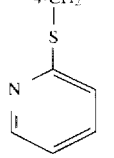 4-CH$_2$-S-(pyridin-2-yl) | H | H | 158 ethyl acetate 2HCl |

TABLE 2
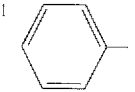
| Product SR (Example no) | m | Z | M.p., °C. Recryst. solvent. Salt |
|---|---|---|---|
| 45303 A (56) | 2 | H | — ether HCl |
| 47122 A (57) | 2 | —CH₃ | 77 ether HCl |
| 45599 A (58) | 2 | —CH₂CH₃ | 170 ether HCl |
| 47315 A (59) | 2 | —CH—(CH₃)₂ | 170 ether HCl |
| 47581 A (60) | 3 | —CH—(CH₃)₂ | 150 isopropyl ether HCl |
| 47314 A (61) | 2 | —C—(CH₃)₃ | 160 ether HCl |
| 45946 A (62) | 2 | —CH₂—(CH₂)₂—CH₂CH₃ | 188 ether HCl |
| 47144 A (63) | 1 |  | 82-84 ether HCl |
| 45305 A (64) | 2 | 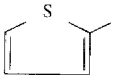 | 160 ether HCl.0.5 H₂O |
| 47242 A (65) | 3 | 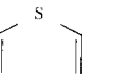 | 122 ether HCl |
| 47989 A (66) | 3 | 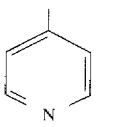 | 104 isopropyl ether HCl |
| 45947 A (67) | 2 | 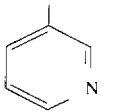 | 166 ether 2HCl |
| 47721 A (68) | 3 | 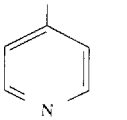 | 170 AcOEt HCl |
| 47720 A (69) | 3 |  | 185 AcOEt HCl |

TABLE 2-continued

Structure: Ph-CH₂-(piperidine)-N-(CH₂)ₘ-CH-CH₂-N(H)-C(=O)-Z, where the CH bears a 3,4-dichlorophenyl group

| Product SR (Example no) | m | Z | M.p., °C. Recryst. solvent. Salt |
|---|---|---|---|
| 47909 A (70) | 2 | 3-methylisoxazol-5-yl (O–N=C(CH₃)–CH=C–) | 104 ether HCl |
| 48043 A (71) | 3 | 3-methylisoxazol-5-yl | 92 isopropyl ether HCl |
| 46695 A (72) | 2 | 2-methyl-3-phenyl-1-oxo-1H-inden-yl | 100 (decomposition) ether HCl |
| 46212 A (73) | 2 | naphthalen-1-yl (8-methyl) | 218 ether HCl |
| 47341 A (74) | 2 | naphthalen-2-yl (substituted) | 224 acetone HCl |
| 46669 A (75) | 2 | 4-fluoro-1-methylnaphthalen-yl | 210 acetone HCl |
| 46673 A (76) | 2 | quinolin-8-yl | 158 ethyl acetate 2HCl |
| 45880 A (77) | 2 | –CH₂–(2,4-dichlorophenyl) | 114–116 ether HCl |
| 45841 A (78) | 2 | –CH₂–(4-hydroxyphenyl) | 146 ether HCl |
| 45792 A (79) | 2 | –CH₂–CH₂–phenyl | 110 ether HCl |

TABLE 2-continued

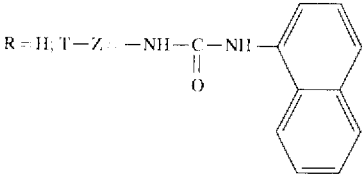

| Product SR (Example no) | m | Z | M.p., °C. Recryst. solvent. Salt |
|---|---|---|---|
| 45869 A (80) | 2 | —CH=CH—⬡ | 90–92 CH₂Cl₂/ether HCl |
| 46215 A (81) | 2 | —CH₂-(1-naphthyl) | 145 ether HCl |
| 46213 A (82) | 2 | —CH₂-(2-naphthyl) | 125 ether HCl |
| 46028 A (83) | 2 | —CH₂-(4-pyridyl) | 174 ether 2HCl |
| 46389 A (84) | 2 | —CH₂—S-(2-pyridyl) | 128 ethyl acetate 2HCl |
| 46294 A (85) | 2 | —CH₂—S-(4-pyridyl) | 168 ether 2HCl |
| 45793 A (86) | 3 | H | 130 ether HCl |

EXAMPLE 87

N'-[4-(4-Benzylpiperidin-1-yl)-2-(3,4-dichlorophenyl)butyl]-N-naphth-1-ylurea hydrochloride. SR 45924 A (I):

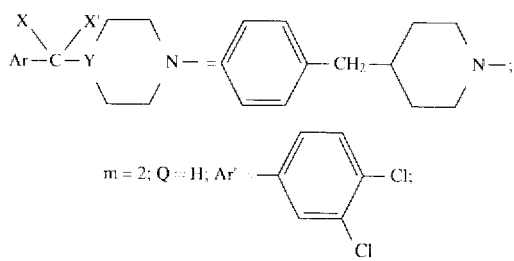

m = 2; Q = H; Ar' = 3,4-dichlorophenyl;

-continued

R = H; T—Z = —NH—C(=O)—NH-(naphth-1-yl)

2.52 g of 1-amino-4-(4-benzylpiperidin-1-yl)-2-(3,4-dichlorophenyl)butane are dissolved in 30 ml of anhydrous benzene, 1.09 g of naphth-1-yl isocyanate are then added and the reaction mixture is stirred overnight at room temperature. The excess isocyanate is decomposed by adding 10 ml of methanol and heating the mixture at the boil for 30 minutes.

The mixture is concentrated under vacuum and the residue is taken up in an ethyl acetate/water mixture, washed with a 10% solution of sodium hydroxide and then water, decanted, dried over MgSO$_4$ and concentrated under vacuum. The residue is taken up in acetone, a solution of hydrogen chloride in ether is then added and the hydrochloride is filtered off and solidified in ether.

m=3.3 g

M.p.=174° C.

The compounds described in Table 3 were prepared according to Example 87.

TABLE 3

Structure: Ph–CH$_2$–(piperidine)–N–(CH$_2$)$_m$–C(H)(Ar')–CH$_2$–NH–C(=W)–NH–Z

| Product SR no (Example no) | m | Ar' | Z | W | M.p., °C. Recryst. solvent. Salt |
|---|---|---|---|---|---|
| 45924 B (87b) | 2 | 3,4-dichlorophenyl | 1-naphthyl | O | 158 ether methanesulfonate hemihydrate |
| 45924 C (87c) | 2 | 3,4-dichlorophenyl | 1-naphthyl | O | 138 ether glycolate |
| 45924 D (87d) | 2 | 3,4-dichlorophenyl | 1-naphthyl | O | 124 ethyl acetate gluconate |
| 45924 E (87e) | 2 | 3,4-dichlorophenyl | 1-naphthyl | O | 148 hexane trifluoroacetate |
| 45924 F (87f) | 2 | 3,4-dichlorophenyl | 1-naphthyl | O | 138 ether isethionate |
| 45923 A (88) | 2 | 3,4-dichlorophenyl | 2,4-dichlorophenyl | O | 182 ether HCl |
| 45308 A (89) | 2 | 3,4-dichlorophenyl | CH$_2$–phenyl | O | 120 ether HCl.0.5 H$_2$O |

TABLE 3-continued

General structure:

Phenyl-CH₂-(piperidine)-N-(CH₂)ₘ-C(H)(Ar')-CH₂-NH-C(=W)-NH-Z

| Product SR no (Example no) | m | Ar' | Z | W | M.p., °C Recryst. solvent. Salt |
|---|---|---|---|---|---|
| 45673 A (90) | 2 | 1-naphthyl | CH₂-phenyl | O | 105–107 ether/isopropanol HCl.H₂O |
| 45671 A (91) | 2 | 3,4-dichlorophenyl | 4-chlorophenyl | S | 96–98 hexane methanesulfonate |
| 46670 A (92) | 2 | 3,4-dichlorophenyl | 1-naphthyl | S | 178 ether HCl |
| 45903 A (93) | 3 | 3,4-dichlorophenyl | CH₂-phenyl | O | 135 ether HCl |
| 46987 A (94) | 2 | 3,4-dichlorophenyl | 4-(COCH₃)phenyl | O | 225 ether hydrochloride |
| 46986 A (95) | 2 | 3,4-dichlorophenyl | 2,6-dichloropyridin-4-yl | O | 215 ether hydrochloride |

EXAMPLE 96

Benzyl N-[4-(4-benzylpiperidin-1-yl)-2-(3,4-dichlorophenyl)butyl]carbamate hydrochloride. SR 46940 A (I):

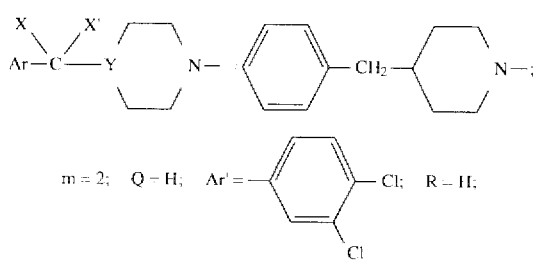

m = 2; Q = H; Ar' = 3,4-dichlorophenyl; R = H;

-continued

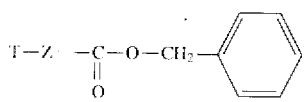

T—Z : —C(=O)—O—CH₂-phenyl 2.26 g of 1-amino-4-(4-benzylpiperidin-1-yl)-2-(3,4-dichlorophenyl)butane hydrochloride and 0.89 g of benzyl chloroformate are dissolved in 30 ml of methylene chloride. The mixture is cooled to 0° C. and a solution of 1.52 g of triethylamine in 10 ml of methylene chloride is then added. The reaction mixture is left for 1 hour at room temperature and then concentrated under vacuum. The residue is taken up in water, extracted with ethyl acetate, washed with a 10% solution of sodium hydroxide and then a saturated solution of sodium chloride, dried over MgSO₄ and concentrated under vacuum. The residue is chromatographed on silica gel

EXAMPLE 97

Ethyl N-[4-(4-benzylpiperidin-1-yl)-2-(3,4-dichlorophenyl)butyl]carbamate hydrochloride (I):

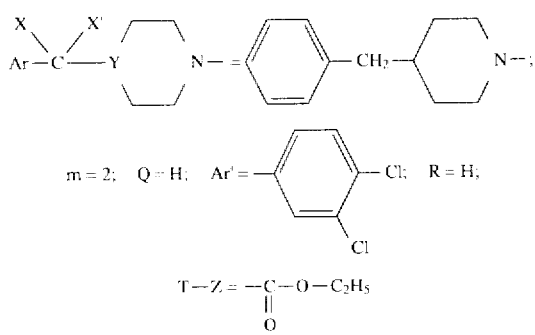

m=2; Q=H; Ar'= (3,4-dichlorophenyl); R=H;

T—Z = —C—O—C$_2$H$_5$
         ‖
         O 9.8 g of 1-amino-4-(4-benzylpiperidin-1-yl)-2-(3,4-dichlorophenyl)butane dihydrochloride and 6.7 g triethylamine are dissolved in 200 ml of methylene chloride. 2.28 g of ethyl chloroformate are added dropwise to this solution at room temperature and the reaction mixture is left to stand for one hour at room temperature, with stirring. The reaction mixture is concentrated under vacuum and the residue is taken up in ethyl acetate/water and washed successively with a 5% solution of sodium hydroxide, water and a saturated solution of sodium chloride. The organic phase is dried over Na$_2$SO$_4$ and concentrated under vacuum to give a residue, which is chromatographed on silica gel using a 94/6 methylene chloride/methanol mixture as the eluent. Concentration of the pure fractions gives residue, which is taken up in ethyl acetate. A solution of hydrogen chloride in ether is added to the ethyl acetate solution and the hydrochloride is filtered off.

m=6.5 g
M.p.=108°–110° C.

EXAMPLE 98

N-Methyl-N-[4-(4-benzylpiperidin-1-yl)-2-(3,4-dichlorophenyl)butyl]-2,4-dichlorobenzamide hydrochloride. SR 46650 A (I):

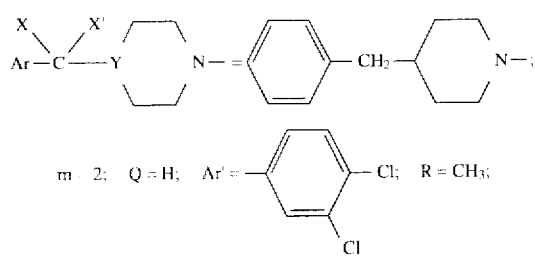

m=2; Q=H; Ar'= (3,4-dichlorophenyl); R=CH$_3$;

-continued

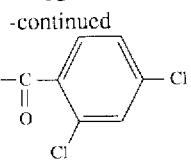

T—Z = —C—(2,4-dichlorophenyl)
         ‖
         O a) 4-(4-Benzylpiperidin-1-yl)-2-(3,4-dichlorophenyl)-1-N-methylaminobutane hydrochloride 6.5 g of the product obtained in Example 97 and 1.6 g of lithium aluminum hydride are dissolved in 150 ml of tetrahydrofuran and refluxed for 3 hours. The reaction mixture is hydrolyzed by the addition of a 2N solution of sodium hydroxide and then filtered on Célite. The filtrate is concentrated under vacuum, the residue is taken up in ethyl acetate and the hydrochloride is obtained by the addition of a solution of hydrogen chloride in ether.

m=4.3 g
M.p.=234°–236° C.

b) SR 46650 A

SR 46650 A is obtained by reacting 2,4-dichlorobenzoyl chloride with the product obtained above, following the procedure described in Example 1.

M.p.=140°–142° C.

EXAMPLE 99

N-(1-Aminohexyl)-N-[4-(4-benzylpiperidin-1-yl)-2-(3,4-dichlorophenyl)butyl]-2,4-dichlorobenzamide dihydrochloride hemihydrate. SR 46510 A (I):

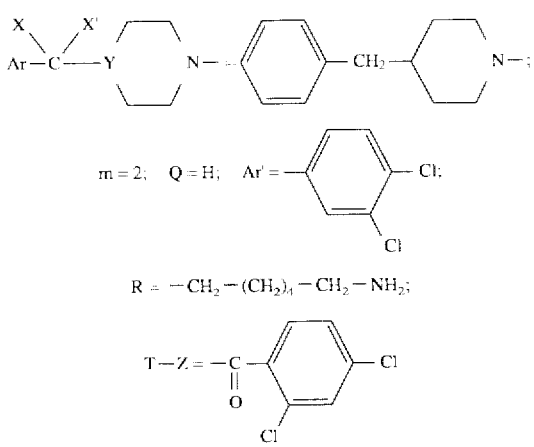

m=2; Q=H; Ar'= (3,4-dichlorophenyl);

R = —CH$_2$—(CH$_2$)$_4$—CH$_2$—NH$_2$;

T—Z = —C—(2,4-dichlorophenyl)
         ‖
         O a) 4-(4-Benzylpiperidin-1-yl)-2-(3,4-dichlorophenyl)-1-N-tritylaminopentylamidobutane 3 g of 1-amino-4-(4-benzylpiperidin-1-yl)-2-(3,4-dichlorophenyl)butane hydrochloride are suspended in 60 ml of methylene chloride in the presence of 3.2 ml of triethylamine. After the diamine has dissolved, 2.5 g of tritylaminocaproic acid and then 3.2 g of BOP are added. The reaction mixture is stirred at room temperature for 30 minutes, washed with water, a dilute solution of sodium hydroxide and then water, decanted, dried over MgSO$_4$, filtered and concentrated under vacuum. The residue is chromatographed on silica gel using a 95/5 methylene chloride/methanol mixture as the eluent. Concentration of the pure fractions gives 3.6 g of the expected product.

b) 4-(4-Benzylpiperidin-1-yl)-2-(3,4-dichlorophenyl)-1-N-(1-tritylaminohexyl)aminobutane 3.6 g of the product obtained above are dissolved in 40 ml of tetrahydrofuran and added dropwise to a suspension of 600 mg of lithium aluminum hydride in 20 ml of tetrahydrofuran. The reaction mixture is refluxed for 18 hours and then cooled, hydrolyzed, filtered and concentrated under vacuum. The residue is chromatographed on silica gel using an 80/20 methylene chloride/methanol mixture as the eluent. Concentration of the pure fractions gives 1.9 g of the expected product.

c) N-[4-(4-Benzylpiperidin-1-yl)-2-(3,4-dichlorophenyl)-N-(1-tritylaminohexyl)aminobutyl]-2,4dichlorobenzamide 1.9 g of the product obtained above are dissolved in 30 ml of methylene chloride. The solution is cooled to –20° C. and 0.57 g of 2,4-dichlorobenzoyl chloride in 10 ml of methylene chloride is then added. The mixture is left to return to room temperature, washed twice with water, decanted, dried over MgSO$_4$ and concentrated under vacuum. The residue is chromatographed on silica gel using a 95/5 methylene chloride/methanol mixture as the eluent. Concentration of the pure fractions gives 1.5 g of the expected amide.

d) SR 46510 A 1.5 g of the tritylated derivative obtained above are dissolved in 15 ml of a 50% solution of formic acid in water and stirred at 60° C. for one hour. The cooled mixture is filtered and the filtrate is concentrated under vacuum. The residue is taken up in water, washed with ether, rendered alkaline with sodium hydroxide, extracted with methylene chloride, decanted, dried over MgSO$_4$ and concentrated under vacuum. The residue obtained is taken up in 5 ml of methylene chloride, and a solution of hydrogen chloride in ether is added until the pH is 1.

m=1 g

M.p.=100° C. (decomposition).

TABLE 4

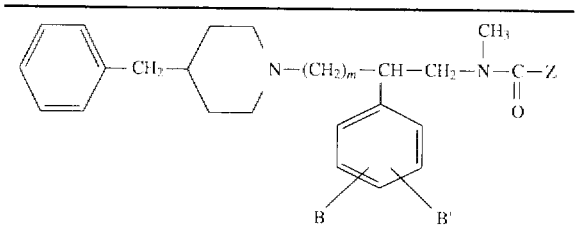

| SR n° Example n° | m | B | B' | Z | Elemental analysis C H N Calculated % Found % or M.p. °C. and Salt |
|---|---|---|---|---|---|
| 47827 A (100) | 2 | 3-Cl | 4-Cl | O | 60.70 6.37 5.05<br>60.73 6.75 4.93<br>HCl. H$_2$O |
| 47852 A (101) | 2 | H | 3-F | S | 88<br>HCl |
| 47239 A (102) | 2 | 3-Cl | 4-Cl | S | 59.94 6.10 4.99<br>59.84 6.10 4.85<br>HCl. 0.5 H$_2$O |

TABLE 4-continued

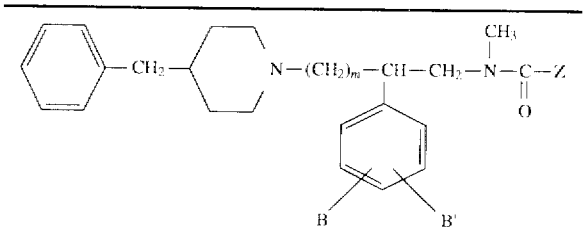

| SR n° Example n° | m | B | B' | Z | Elemental analysis C H N Calculated % Found % or M.p. °C. and Salt |
|---|---|---|---|---|---|
| 47829 A (103) | 2 | 3-Cl | 4-Cl | S | 59.94 6.10 4.99<br>59.83 6.30 4.77<br>HCl. 0.5 H$_2$O |
| 47241 A (104) | 3 | 3-Cl | 4-Cl | S | 60.57 6.31 4.87<br>60.88 6.47 4.74<br>HCl. 0.5 H$_2$O |
| 47828 A (105) | 2 | 3-Cl | 4-Cl |  | 64.92 6.54 5.04<br>64.59 6.77 4.88<br>HCl. 0.5 H$_2$O |
| 47240 A (106) | 3 | 3-Cl | 4-Cl |  | 58.36 5.68 4.39<br>Cl 58.46 5.65 4.68<br>HCl. 0.5 H$_2$O |

EXAMPLE 107

N-[4-(4-Benzylpiperidin-1-yl)-2- (3,4-dichlorophenyl)-2-isobutylbutyl]-2,4-dichlorobenzamide hydrochloride. SR 46753 A (I):

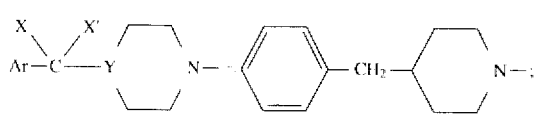

m = 2; Q = —CH$_2$—CH—(CH$_3$)$_2$; Ar' = 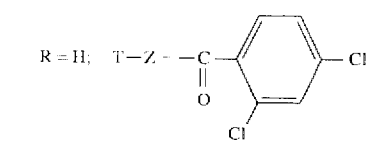

a)  4-(4-Benzylpiperidin-1-yl)-2-(3,4-dichlorophenyl)-2-isobutylbutyronitrile 6 g of 4-(4-benzylpiperidin-1-yl)-2-(3,4-dichlorophenyl)butyronitrile are dissolved in 70 ml of anhydrous ether in the presence of 0.62 g of sodium amide. The reaction mixture is refluxed for 2 hours and then left to return to room temperature and 2.12 g of 1-bromo-2-methylpropane are added. The reaction mixture is refluxed for 24 hours and concentrated under vacuum. The residue is taken up in water, extracted with ethyl acetate, decanted, dried over $MgSO_4$, filtered and concentrated under vacuum.

The expected product is obtained after purification by chromatography on silica gel using a 90/10 hexane/ethyl acetate mixture as the eluent.

b)  1-Amino-4-(4-benzylpiperidin-1-yl)-2-(3,4-dichlorophenyl)-2-isobutylbutane 2.6 g of the product obtained above are dissolved in a mixture of 30 ml of ammonia and 20 ml of water. A catalytic amount of Raney nickel is added and hydrogenation is carried out at atmospheric pressure and at room temperature. The catalyst is filtered off and the filtrate is concentrated under vacuum. The residue is taken up in methanol and the hydrochloride is obtained by the addition of a solution of hydrogen chloride in ether.

c) SR 46753 A

SR 46753 A is obtained by reacting the product obtained above with 2,4-dichlorobenzoyl chloride, as described in Example 1.

M.p.=126° C.

The compounds described in Table 5 were synthesized according to Example 107.

In the formula below, the group Ar' indicated in Formula I is a 3,4-dichlorophenyl group and the group Z is a 2,4-dichlorophenyl group.

TABLE 5

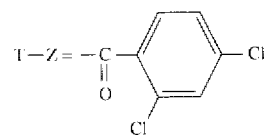

| Product SR n° (Example n°) | Q | M.p., °C. Recryst. solvent. Salt |
|---|---|---|
| 46507 A (108) | —(CH₂)₃—N(CH₃)(CH₃) | 145–157 methylene chloride/ether 2HCl |
| 46754 A (109) | —(CH₂)₂—N(piperidinyl)—CH₂-phenyl | 124 pentane/ether 2HCl.H₂O |
| 46566 A (110) | —(CH₂)₃—N(piperidinyl) | 135–144 methylene chloride/ether 2HCl.H₂O |

EXAMPLE 111

N-[4-(4-Benzoylpiperidin-1-yl)-2-(3,4-dichlorophenyl)butyl]-2,4-dichlorobenzamide hydrochloride. SR 46159 A (I):

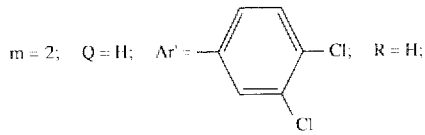

a)  3-(3,4-Dichlorophenyl)-1-(tetrahydropyran-2-yloxy)-3-nitrilopropane 20 g of sodium hydride as a 55–60% dispersion in oil are suspended in 200 ml of dry tetrahydrofuran. A solution of 85 g of 3,4-dichlorophenylacetonitrile in 500 ml of tetrahydrofuran is added dropwise at 20° C., in 30 minutes, and the reaction mixture is then stirred at room temperature for 2 hours. The mixture is cooled to −20° C., a solution of 98 g of 1-bromo-2-tetrahydropyranylethanyloxyethane in 100 ml of tetrahydrofuran is added, the mixture is left to return to room temperature and, after 2 hours, a solution of 50 g of ammonium chloride in 3 liters of water is added. The mixture is extracted with 1.5 liters of ether, washed with a saturated solution of sodium chloride, decanted, dried over $MgSO_4$ and concentrated under vacuum.

The residue is chromatographed on silica gel using methylene chloride as the eluent. The pure product fractions are concentrated under vacuum to give 83.6 g of an oil.

b)  1-Amino-2-(3,4-dichlorophenyl)-4-(tetrahydropyran-2-yloxy)butane 83.6 g of the nitrile obtained above are dissolved in 100 ml of absolute ethanol. 350 ml of concentrated ammonia are added and Raney nickel (10% of the amount of starting amine) is then added while sweeping with nitrogen. Hydrogenation is then carried out under a hydrogen atmosphere at room temperature and ordinary pressure.

11.9 liters of hydrogen are absorbed in 3 hours. The catalyst is filtered off on Célite, the filtrate is concentrated under vacuum and the residue is taken up in a saturated solution of sodium chloride. 82.5 g of an oil are obtained after extraction with ether and drying over $MgSO_4$.

c) 1-(2,4-Dichlorobenzoylamino)-2-(3,4-dichlorophenyl)-4-(tetrahydropyran-2-yloxy)butane 80 g of the amine obtained above are dissolved in 800 ml of methylene chloride. The solution is cooled to 0° C. and 38.4 ml of triethylamine and then 55 g of 2,4-dichlorobenzoyl chloride are added. The reaction mixture is subsequently stirred at room temperature for one hour and then washed with water. The organic phase is decanted, dried over $MgSO_4$ and concentrated under vacuum to give 120 g of an oil.

d) 1-(2,4-Dichlorobenzoylamino)-2-(3,4-dichlorophenyl)butan-4-ol 120 g of the product obtained above are dissolved in 1 liter of methanol in the presence of 12 g of paratoluenesulfonic acid. The reaction mixture is stirred for 18 hours at room temperature and then concentrated under vacuum. The residue is taken up in methylene chloride and washed with a 10% solution of sodium carbonate. The organic phase is decanted and dried over MgSO$_4$ to give 106 g of an oil.

e) 1-(2,4-Dichlorobenzoylamino)-2-(3,4-dichlorophenyl)-4-mesyloxybutane 106 g of the alcohol obtained above are dissolved in 1 l of methylene chloride, the solution is cooled to 0° C. and 44 ml of triethylamine and 24.2 ml of mesyl chloride are then added. The reaction mixture is stirred at 0° C. for 45 minutes, washed 3 times with iced water, decanted, dried over MgSO$_4$ and concentrated under vacuum.

The residue is recrystallized from isopropyl ether.
m=95 g.

f) SR 46159 A 3 g of the mesylate obtained above and 3.1 g of 4-benzoylpiperidine are dissolved in 7 ml of methylene chloride and the reaction mixture is refluxed for 24 hours. The mixture is diluted in methylene chloride and washed with water, then with a dilute solution of sodium hydroxide and then again with water. The organic phase is decanted, dried over MgSO$_4$ and concentrated under vacuum. The residue is chromatographed on silica gel using a 70/30 methylene chloride/methanol mixture as the eluent.

The pure product fractions are concentrated under vacuum, the residue is diluted in methylene chloride and the hydrochloride is obtained by the addition of a solution of hydrogen chloride in ether.

m=930 mg.

CHN: Calculated % 55.83 4.84 4.49
C$_{29}$H$_{28}$Cl$_4$N$_2$O$_2$.HCl.O.5H$_2$O: Found % 55.69 4.97 4.71

The compounds of the Examples listed in Table 6 (I, Ar'=3,4-dichlorophenyl; Z=2,4-dichlorophenyl) were prepared according to Example 111.

The compounds of the Examples listed in Table 7 (I, Ar'=3,4-dichlorophenyl) and Table 8 (I, Ar'=3,4-dichlorophenyl or 3-trifluoromethylphenyl ) were prepared according to Example 1, 2 or 3.

TABLE 6

TABLE 6-continued

[Structure: Ar-C(X)(X')-Y-N(piperazine ring)-CH₂-CH₂-CH(Ar')-CH₂-NH-C(=O)-(2,4-dichlorophenyl), where Ar' = 3,4-dichlorophenyl]

| Product SR n° (Example n°) | Ar-C(X)(X')-Y-N⟩ group | Elemental analysis Calculated % / Found % / Salt % | C | H | N |
|---|---|---|---|---|---|
| 46509 A (116) | 4-CF₃-phenyl-C(=O)-piperidine-N- | | 52.76 / 52.52 / HCl | 4.13 / 4.26 | 4.10 / 3.97 |
| 46619 A (117) | 4-F-phenyl-C(=N-OCH₂CH₂-N(CH₃)₂)-piperazine-N- | | 51.84 / 51.72 / HCl·0.5 H₂O | 5.27 / 5.53 | 7.32 / 7.09 |
| 46690 A (118) | phenyl-CH₂-piperazine-N- | | 52.68 / 52.06 / 2 HCl | 4.90 / 5.02 | 6.58 / 6.42 |
| 47147 (119) | phenyl-C(=O)-piperazine-N- | | 53.82 / 53.61 / HCl·0.5 H₂O | 4.68 / 4.72 | 6.72 / 6.46 |
| 47678 A (120) | imidazole-CH₂-piperidine-N- | | 48.39 / 48.21 / 2HCl·H₂O | 5.00 / 5.23 | 8.68 / 8.28 |
| 46261 A (121) | thiophene-CH₂-piperidine-N- | | 52.68 / 52.91 / HCl·0.5 H₂O | 4.91 / 5.01 | 4.55 / 4.47 |
| 46445 A (122) | thiophene-C(=O)-piperidine-N- | | 52.23 / 51.89 / HCl·0.5 H₂O | 4.38 / 4.53 | 4.51 / 4.33 |

TABLE 6-continued
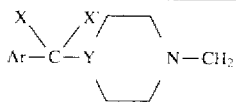
| Product SR n° (Example n') | 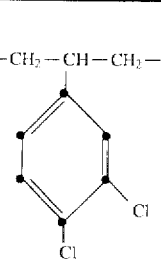 | Elemental analysis Calculated % Found % Salt % | C | H | N |
|---|---|---|---|---|---|
| 46158 A (123) | 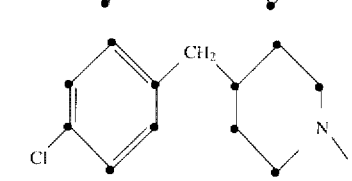 | HCl.0.5 H$_2$O | 55.47<br>55.57 | 4.97<br>4.97 | 4.46<br>4.43 |
| 46157 A (124) | 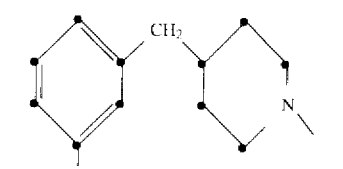 | HCl.0.5 H$_2$O | 54.05<br>54.10 | 4.84<br>4.91 | 4.34<br>4.28 |
| 46511 A (125) | 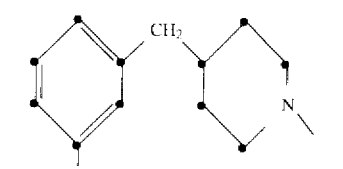 | HCl | 53.87<br>53.69 | 4.52<br>4.75 | 4.19<br>4.05 |
| 46288 A (126) |  | HCl.0.5 H$_2$O | 56.30<br>55.91 | 5.35<br>5.29 | 4.39<br>4.56 |
| 47348 A (127) | 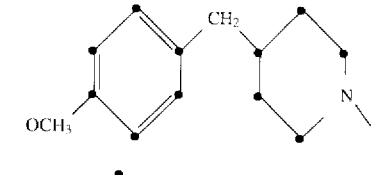 | 2HCl.H$_2$O | 49.73<br>50.13 | 4.74<br>4.72 | 6.00<br>5.84 |

TABLE 7
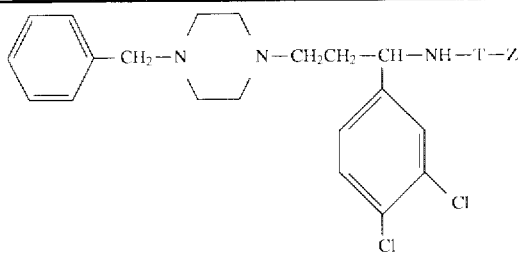
| SR n° Example n° | T—Z | Calculated % Found % Salt | C | H | N |
|---|---|---|---|---|---|
| 46924 A (128) | —CO—C₆H₄—CN (meta) | | 57.71<br>57.85<br>2HCl.0.5 H₂O | 5.47<br>5.59 | 9.28<br>9.08 |
| 46925 A (129) | —CO—C₆H₄—CN (para) | | 57.71<br>57.80<br>2HCl.0.5 H₂O | 5.47<br>5.41 | 9.28<br>9.21 |
| 46913 A (130) | —CO—C₆H₄—NH₂ (ortho) | | 52.63<br>52.19<br>3HCl.H₂O | 5.84<br>6.07 | 8.77<br>8.32 |
| 46922 A (131) | —CO—C₆H₃(NH₂)(Cl) | | 50.61<br>51.01<br>2HCl.0.5 H₂O | 5.31<br>5.45 | 8.43<br>8.21 |
| 46915 A (132) | —CO—C₆H₃(NH₂)(Cl) | | 50.61<br>50.30<br>3HCl.0.5 H₂O | 5.31<br>5.48 | 8.43<br>8.16 |
| 46813 A (133) | —CO—NH—naphthyl | | 58.90<br>58.62<br>3HCl.H₂O | 5.83<br>6.01 | 8.54<br>8.42 |

TABLE 8

Structure: Ph-CH₂-(piperidine)-N-(CH₂)ₘ-CH(Ar')-CH₂-NH-C(=O)-Z

| Product SR n° (Example n°) | m | Ar' | Z | M.p., °C. Recryst. solvent. Salt |
|---|---|---|---|---|
| 46721 A (134) | 2 | 3,4-dichlorophenyl | 2-methylphenyl-S-(3,5-dimethoxyphenyl)-N | 120–125 ether 2HCl |
| 46827 A (135) | 2 | " | 3,4-dimethyl-5-phenyl-isoxazol-yl ($H_5C_6$) | 107–110 $CH_2Cl_2$/isopropyl ether HCl |
| 46890 A (136) | 2 | " | 3-methyl-chromon-2-yl | 118–123 $CH_2Cl_2/Et_2O$ HCl |
| 47099 A (137) | 2 | " | 2,6-dichloropyridin-4-yl | 120–130 $CH_2Cl_2/Et_2O$ HCl |
| 47157 A (138) | 2 | 3-trifluoromethylphenyl | 3,4-dimethyl-5-phenyl-isoxazolyl ($H_5C_6$) | 112 Pentane/$Et_2O$ HCl |
| 47221 A (139) | 2 | 3,4-dichlorophenyl | N—N—$C_6H_5$ / =N / CH(CH₃) | 170–174 $CH_2Cl_2$/isopropyl ether HCl |
| 47284 A (140) | 2 | " | 3-(2-chlorophenyl)-4,5-dimethyl-isoxazolyl | 122 $CH_2Cl_2/Et_2O$ HCl |

TABLE 8-continued

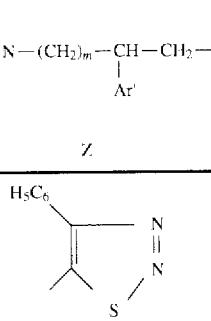

| Product SR n° (Example n°) | m | Ar' | Z | M.p., °C. Recryst. solvent. Salt |
|---|---|---|---|---|
| 47437 A (141) | 2 | " | 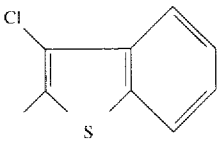 | 98-100 ether HCl |
| 47806 A (142) | 2 | " | 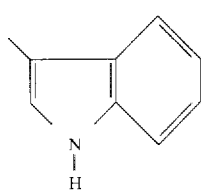 | 124 isopropyl ether/CH₂Cl₂ HCl |
| 47036 A (143) | 2 | " | 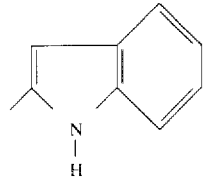 | 159–161 AcOEt HCl |
| 46769 A (144) | 2 | " | 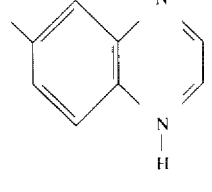 | 153–155 CH₂Cl₂/Ether HCl |
| 47000 A (145) | 2 | " | 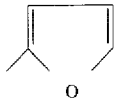 | 200 AcOEt HCl |
| 47580 A (146) | 3 | " | 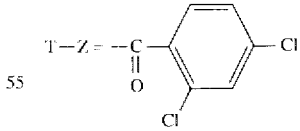 | 180 isopropyl ether HCl |

EXAMPLE 147

N-[4-(4-Benzylpiperidin-1-yl)-2-(3,4-dichlorophenyl)butyl]-2,4-dichlorobenzamide (+) hydrochloride. SR 47050 A (I*):

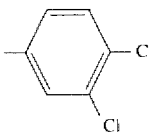

m = 2; Q = H; Ar' = 3,4-dichlorophenyl; R = H;

T—Z = 2,4-dichlorobenzoyl

The optical rotations of the compounds below were measured at 25° C.

A) N-(1-Phenylethyl)-β-(tert-butoxycarbonylaminomethyl)-3,4-dichlorobenzenepropionamide Step 1

A solution of 39.6 ml of diisopropylamine in 200 ml of anhydrous THF is introduced into a 2-liter three-necked flask swept with nitrogen. The solution is cooled to –60° C. and the following are added in order at this temperature:

176 ml of a 1.6M solution of butyllithium in hexane, 50 g of 3,4-dichlorobenzeneacetonitrile in 300 ml of THF, and then 39.4 ml of tert-butyl bromoacetate in 100 ml of THF.

The mixture is left to return to a temperature of 0° C. in 2 hours 30 minutes. It is poured into 3 l of a saturated aqueous solution of ammonium chloride. The mixture is extracted twice with ether and dried over magnesium sulfate and the solvents are evaporated off. The oil obtained is chromatographed on 1 kg of silica H using a 95/5 cyclohexane/ethyl acetate mixture as the eluent. This gives 44.3 g of tert-butyl β-cyano-3,4-dichlorobenzenepropionate.

M.p.=67° C.

Step 2

A mixture of 40 g of the product obtained above (Step 1), 700 ml of absolute ethanol, 200 ml of concentrated ammonia (20%) and 3 spatulas of Raney nickel is stirred under a hydrogen atmosphere for 5 hours. After filtration of the catalyst and evaporation of the solvents, 38.8 g of tert-butyl β-aminomethyl-3,4-dichlorobenzenepropionate are obtained in the form of an oil.

Step 3

A solution of 23.5 g of the product obtained above (Step 2) in 150 ml of methylene chloride is cooled to −10° C. 250 ml of trifluoroacetic acid are added and the mixture is then left to return to a temperature of 20° C. in 1 h 30 min.

After removal of the solvents, 27 g of β-amino-methyl-3,4-dichlorobenzenepropionic acid trifluoroacetate are obtained in the form of an oil.

Step 4

150 ml of dioxane, then 30 ml of triethylamine and then a solution of 23 g of ditert-butyl dicarbonate in 50 ml of dioxane are added to a solution of 27 g of the product obtained above (Step 3) in 150 ml of water. The mixture is heated at 100° C. for 1 hour. The dioxane is removed under vacuum and the solution obtained is washed with isopropyl ether. The aqueous phase is poured into 1.5 l of a phosphate buffer solution of pH 2. After extraction with ether and drying over magnesium sulfate, the solvents are evaporated off. The oil obtained is crystallized from isopropyl ether to give 20.3 g of β-(tert-butoxycarbonylaminomethyl)-3,4-dichlorobenzenepropionic acid.

Step 5

The following are added in order to a solution of 10 g of the product obtained above (Step 4) in 150 ml of methylene chloride:

8 ml of triethylamine, 3.5 g of S(−)-α-methylbenzylamine, and 14 g of BOP (benzotriazolyl-N-oxytrisdimethylaminophosphonium hexafluorophosphate).

After stirring at room temperature for 1 hour, the mixture is washed with water, then with a phosphate buffer solution of pH 2 and then with a saturated aqueous solution of sodium bicarbonate. It is dried over magnesium sulfate and the solvents are removed under vacuum to give 12 g of N-(1-phenylethyl)-β-(tert-butoxycarbonylaminomethyl)-3,4-dichlorobenzenepropionamide.

B) Methyl ester of β-(2,4-dichlorobenzoylaminomethyl)-3,4-dichlorobenzenepropionic acid (+)

Step 1

Separation of the diastereoisomers of N-(1-phenylethyl)-β-(tert-butoxycarbonylaminomethyl)-3,4dichlorobenzenepropionamide The crude product is a mixture of two diastereoisomers. They can be separated by thin layer chromatography. They are separated preparatively by means of chromatography on 400 g of silica H using an 20 toluene/ethyl acetate mixture as the eluent. The less polar isomer emerges first and 5.8 g thereof are collected.

M.p.=146°–147° C.

$[\alpha]_D$=−43.6° (c=1 in chloroform).

Step 2

A solution of 5 g of the product obtained above in 10 ml of dioxane and 50 ml of 6N hydrochloric acid is refluxed overnight. After cooling, the solution is washed with ether and the aqueous phase is then progressively neutralized with solid sodium bicarbonate until the pH is 7. This gives a precipitate, which is filtered off and washed with water, isopropanol and then ether. After drying, 1.88 g of β-aminomethyl-3,4-dichlorobenzenepropionic acid are obtained.

M.p.=202°–204° C.

Step 3

1.10 ml of thionyl chloride are added to a suspension of 1.85 g of the product obtained above (Step 2) in 20 ml of methanol, cooled to −20° C. and under nitrogen, and the mixture is then left to return to a temperature of 20° C. 2 hours later, 200 ml of ether are added and the product which has crystallized is filtered off and washed with ether. After drying, 2.15 g of methyl β-aminomethyl-3,4-dichlorobenzenepropionate (−) are obtained.

M.p=184°–186° C.

$[\alpha]_D$=−4.3° (c=1 in methanol).

Step 4

A solution of 2,4-dichlorobenzoyl chloride (1.54 g) in 5 ml of methylene chloride is added to a solution of 2.0 g of the product obtained above (Step 3) and 1.5 g of triethylamine in 20 ml of methylene chloride, cooled to 0° C. 5 min later, the solution is concentrated to dryness, water is added and extraction is carried out with ethyl acetate. The residue obtained is then crystallized from isopropyl ether to give 2.72 g of methyl β-(2,4-dichlorobenzoylaminoethyl)benzenepropionate (+).

M.p.=105°–107° C.

$[\alpha]_D$=+26.6° (c=1 in chloroform).

C) Methyl ester of β-(2,4-dichlorobenzoylaminomethyl)-3,4-dichlorobenzenepropionic acid (−)

Step 1

Following the procedure described in Example 1 B), Step 1, the more polar isomer is collected using an 80/20 and then 60/40 toluene/ethyl acetate mixture as the eluent. Concentration of the fractions gives 5.4 g of N-(1-phenylethyl)-β-(tert-butoxycarbonylaminomethy.)-3,4-dichlorobenzenepropionamide.

M.p.=161°–162° C.

$[\alpha]_D$=−18.4° (c=1 in chloroform).

Step 2

β-Aminomethyl-3,4-dichlorobenzenepropionic acid is prepared following the procedure described in Example 1 B), Step 2.

M.p.=202°–204° C.

Step 3

Methyl β-aminomethyl-3,4-dichlorobenzenepropionate (+) is prepared following the procedure described in Example 1 B), Step 3.

M.p.=184°–185° C.

$[\alpha]_D$=+3.9° (c=1 in methanol).

Methyl β-(2,4-dichlorobenzoylaminomethyl)-3,4dichlorobenzenepropionate (−) is prepared following the procedure described in Example 1 B), Step 4.

M.p.=108°–109° C.

$[\alpha]_D$=−27.7° (c=1 in chloroform).

D) Reduction of the methyl esters of β-(2,4-dichlorobenzoylaminomethyl)-3,4-dichlorobenzenepropionic acid (+) or (−)

First of all, a 0.5M solution of calcium borohydride in THF is prepared by stirring a suspension of sodium borohydride (0.1 mol) and calcium chloride (0.05 mol) in 100 ml of THF for 3 hours. 13 ml of this solution are then added to a solution of 2.5 g of the methyl ester of β-(2,4-dichlorobenzoylaminomethyl)-3,4-dichlorobenzenepropionic acid (+) or (−) in 20 ml of THF. The mixture is stirred overnight. The next day, the solution is cooled to 0° C. and subsequently hydrolyzed with water and then dilute hydrochloric acid. After extraction with ether, the practically pure alcohol (+) or (−) is collected in the form of an oil.

E) Preparation of the mesylate (methanesulfonate) derivatives of γ-(2,4-dichlorobenzoylaminomethyl)-3,4-dichlorobenzenepropanol (+) or (−)

1.3 g of the alcohol obtained above are dissolved in 30 ml of methylene chloride, the solution is cooled to 0° C. and 0.5 ml of triethylamine and 0.3 ml of mesyl chloride are then added. The reaction mixture is stirred at 0° C. for 45 minutes, washed 3 times with iced water, decanted, dried over MgSO₄ and concentrated under vacuum.

The residue is chromatographed on silica gel using a 60/40 ethyl acetate/pentane mixture as the eluent. The pure fractions are concentrated under vacuum.

Thus, starting from the ester (+), a residue is obtained which is recrystallized from isopropyl ether to give 1.1 g of γ-(2,4-dichlorobenzoylaminomethyl)-3,4-dichlorobenzenepropanol (+) methanesulfonate.

M.p.=74°–77° C.

$[\alpha]_D$=+21.2° (c=1 in chloroform).

Thus, starting from the ester (−), γ-(2,4-dichlorobenzoylamimomethyl-3,4-dichlorobenzenepropanol (−) methanesulfonate is obtained following the above procedure.

M.p.=72°–76° C.

$[\alpha]_D$=−22.5° (c=1 in chloroform).

F) Preparation of N-[4-(4-benzylpiperidin-1-yl)-2-(3,4-dichlorophenyl)butyl]-2,4-dichlorobenzamide (+) hydrochloride. SR 47050 A 0.6 g of the mesylate (+) obtained above and 0.54 g of 4-benzylpiperidine are dissolved in 1 ml of dimethylformamide and the reaction mixture is heated at 60° C. for 30 minutes. Water is added and extraction is carried out with ethyl acetate. The organic phase is concentrated under vacuum and the residue is chromatographed on silica gel using a 97/3 methylene chloride/methanol mixture as the eluent.

The pure product fractions are concentrated under vacuum, the residue is diluted in methylene chloride and the hydrochloride is obtained by the addition of a solution of hydrogen chloride in ether.

m=0.5 g $[\alpha]_D$=+14.0° (c=1 in chloroform).

EXAMPLE 148

N-[4-(4-Benzylpiperidin-1-yl)-2-(3,4-dichlorophenyl)butyl]-2,4-dichlorobenzamide (−) hydrochloride. SR 47051 A (I*):

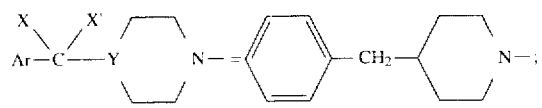

-continued

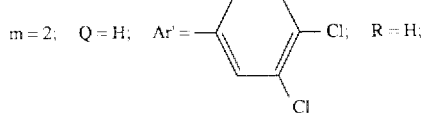

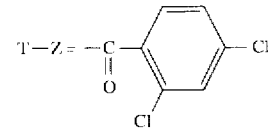

SR 47051 A is obtained following the same procedure as above (according to Example 147 F)), except that the mesylate isomer (−) is used as the starting material.

$[\alpha]_D$=−14.5° (c=1 in chloroform).

EXAMPLE 149

The compound below is prepared following the procedure described in Example 147 above:
N-[4-(4-benzylpiperidin-1-yl)-2-(3,4-difluorophenyl)butyl]-2,4-dichlorobenzamide (−) hydrochloride. SR 47243 A (I*):

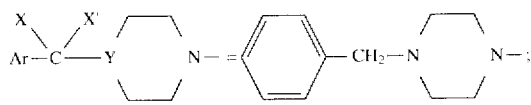

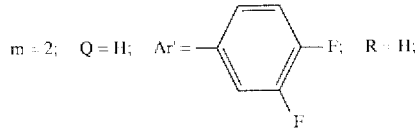

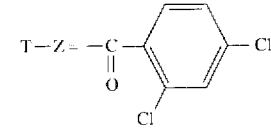

$[\alpha]_D$=−8.5° (c=1 in chloroform).

EXAMPLE 150

The compound below is prepared following the procedure described in Example 147 above:
N-[4-(4-benzylpiperidin-1-yl)-2-(3,4-difluorophenyl)butyl]-2,4-dichlorobenzamide (+) hydrochloride. SR 47238 A (I*):

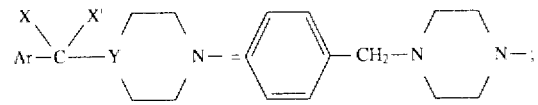

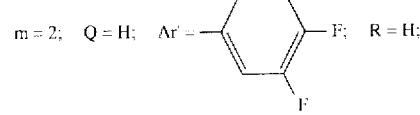

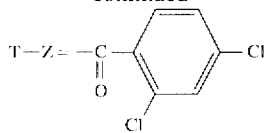

$[\alpha]_D$ 7.3° (c=1 in chloroform).

EXAMPLE 151

N-[4-(4-Benzylpiperidin-1-yl)-2-(3,4-dichlorophenyl)butyl]-4-fluoronaphthalene-1-carboxamide (+) and (−) hydrochloride (I'):

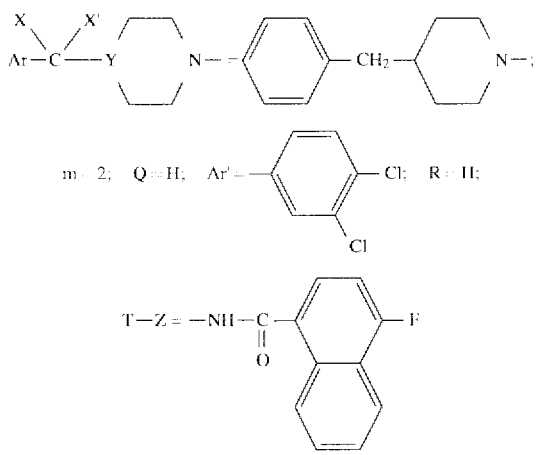

Step 1

1-Amino-2-(3,4-dichlorophenyl)-4-hydroxybutane 150 ml of a saturated solution of hydrogen chloride in ether are added to a solution of 149 g of 4-(tetrahydropyran-2-yloxy)-2-(3,4-dichlorophenyl)-1-aminobutane in 700 ml of methanol. The mixture is stirred for ½ hour at room temperature and concentrated under vacuum and the residue is taken up in 500 ml of water and washed with ether. The aqueous phase is rendered alkaline with a solution of sodium hydroxide and extracted twice with methylene chloride. The organic phases are dried over $MgSO_4$, filtered and concentrated under vacuum. The residue is taken up in 400 ml of isopropyl ether and the mixture is stirred for one hour at room temperature. The precipitate is filtered off and washed with ether.

m=98.2 g
M.p.=90°–91° C.

Step 2

(+)-Enantiomer of 1-amino-2-(3,4-dichlorophenyl)-4-hydroxybutane

A solution of 93 g of the racemate, previously prepared according to Step 1, in 300 ml of methanol is added to a refluxing solution of 59.65 g of D(−)-tartaric acid in 2 liters of methanol. The mixture is left to return to room temperature and the crystals are filtered off, washed with methanol and dried under vacuum at 50° C. over $P_2O_5$.

m=64.8 g
$[\alpha]_D$=−5.2° (c=1 in water).

The product is then recrystallized from 2.96 l of methanol and the crystals are filtered off, washed with methanol and dried under vacuum at 50° C. over $P_2O_5$.

m=45.3 g
$[\alpha]_D$=−4.5° (c=1 in water)
M.p.=201° C.

The D(−)-tartrate is taken up in 250 ml of water, rendered alkaline with a concentrated solution of sodium hydroxide, extracted with 3 times 200 ml of methylene chloride, washed with a saturated solution of sodium chloride, decanted, dried over $MgSO_4$, filtered and concentrated under vacuum. The residue is taken up in isopropyl ether, the mixture is stirred for one hour at room temperature and the crystals are filtered off and washed with isopropyl ether.

m=24.7 g
$[\alpha]_D$=+9.0° (c=1 in methanol)
M.p.=79°–80° C.

(−)-Enantiomer of 1-amino-2-(3,4-dichlorophenyl)-4-hydroxybutane

The (−)-enantiomer is obtained following the above procedure and using L(+)-tartaric acid.

$[\alpha]_D$=−9.2° (c=1 in methanol)
M.p.=79°–80° C.

Step 3

N-[2-(3,4-Dichlorophenyl)-4-mesyloxybutyl]-4-fluoronaphthalene-1-carboxamide ((−)-enantiomer)

A solution of 4.45 g of 4-fluoronaphthoyl chloride in 50 ml of methylene chloride is added dropwise at −60° C. to a solution of 5 g of the product obtained above ((+)-enantiomer) in 100 ml of methylene chloride in the presence of 2.6 g of triethylamine. The mixture is stirred for 15 minutes at −60° C. and left to return to a temperature of −30° C. 2.5 g of triethylamine and 2.7 g of mesyl chloride are then added and the mixture is left to return to room temperature. It is washed with water and the organic phase is dried over $MgSO_4$ and concentrated under vacuum. The residue is chromatographed on silica gel using a 99.5/0.5 methylene chloride/methanol mixture as the eluent.

The pure fractions are concentrated under vacuum.
m=8.4 g
$[\alpha]_D$=−22.8° (c=1 in methanol).

N-[2-(3,4-Dichlorophenyl)-4-mesyloxybutyl]-4-fluoronaphthalene-1-carboxamide (+)-enantiomer)

The (+)-enantiomer is obtained following the procedure described above in Step 3, except that the (−)-enantiomer of Step 2 is used.

$[\alpha]_D$=+22.7° (c=1 in methanol).

Step 4

N-[4-(4-Benzylpiperidin-1-yl)-2-(3,4-dichlorophenyl)butyl]-4-fluoronaphthalene-1-carboxamide hydrochloride. (−)-Enantiomer. SR 48225 A 7 g of the (−)-enantiomer obtained in Step 3 and 5.02M of 4-benzylpiperidine are dissolved in 15 ml of dimethylformamide and the reaction mixture is heated at 70° C. for two hours. The mixture is poured into water and extracted with ethyl acetate and the organic phases are washed with a saturated solution of sodium chloride, dried over $MgSO_4$ and concentrated under vacuum. The residue is chromatographed on silica gel using a 97/3 methylene chloride/methanol mixture as the eluent.

The pure product fractions are concentrated under vacuum, the residue is diluted in methylene chloride and the hydrochloride is obtained by the addition of a solution of hydrogen chloride in ether.

m=6.2 g
$[\alpha]_D$=−35.5° (c=1 in methanol).
(+)-Enantiomer. SR 48226 A

The (+)-enantiomer is obtained following the same procedure as for the (−)-enantiomer prepared above, except that the (+)-enantiomer obtained in Step 3 is used.

m=7 g $[\alpha]_D = +36.0°$ (c=1 in methanol).

EXAMPLE 151:

N-methyl-N [4-(4-benzylpiperidin-1-yl)-2-(3,4-dichlorophenyl)butyl]phenylacetamide hydrochloride. SR 48172A.

The 4-(4-benzylpiperidin-1-yl)-2-(3,4-dichlorophenyl)-1-methyl amino butane hydrochloride obtained in step a) of example 98 is treated with phenylacetic chloride according to the process of example 1, to obtain the compound SR 48172A.

What is claimed is:

1. A stereoselective method of preparing optically pure compounds of formula (I*):

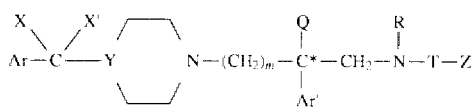

in which:

"*" means that the carbon atom denoted by this symbol has a defined (+) or (−) absolute configuration; and in which:

m is an integer from 1 to 3; Ar and Ar' independently are a thienyl group; a phenyl group which is unsubstituted or mono- or disubstituted by a halogen atom, by a $C_1$-$C_3$ alkyl, by a trifluoromethyl, by an alkoxy in which the alkyl is $C_1$-$C_3$, by a hydroxyl or by a methylenedioxy; or an imidazolyl group; it also being possible for Ar' to be a benzothienyl group which is unsubstituted or substituted by a halogen; a naphthyl group which is unsubstituted or substituted by a halogen; a biphenyl group; or an indolyl which is unsubstituted or substituted on the nitrogen by a benzyl group;

X is hydrogen;

X' is hydrogen or a hydroxyl group or is joined to X" below to form a carbon-carbon bond, or X and X' together form an oxo group or a dialkylamino-alkoxyimino group of the formula =N—O—$(CH_2)_p$—Am, in which p is 2 or 3 and Am is a dialkylamino group, it being possible for each alkyl to contain from 1 to 4 carbon atoms;

Y is a nitrogen atom or a group C(X"), in which X" is hydrogen or forms a carbon-carbon bond with X';

Q is hydrogen, a $C_1$-$C_4$ alkyl group or an aminoalkyl group of the formula —$(CH_2)_q$—Am', in which q is 2 or 3 and Am' is a piperidino, 4-benzylpiperidino or dialkylamino group, it being possible for each alkyl to contain from 1 to 4 carbon atoms;

R is hydrogen, a methyl group or a group $(CH_2)_n$—L, in which n is an integer from 2 to 6 and L is hydrogen or an amino group;

T is a group selected from

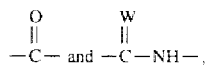

W being an oxygen or sulfur atom; and

Z is either hydrogen, or M or OM when T is the group —C(=O)—, or M when T is the group —C(=W)—NH—, M being hydrogen; a linear or branched $C_1$-$C_6$ alkyl; a phenylalkyl in which the alkyl group contains from 1 to 3 carbon atoms and which is unsubstituted or mono- or poly-substituted on the aromatic ring by a halogen, a hydroxyl, an alkoxy having 1 to 4 carbon atoms or an alkyl having 1 to 4 carbon atoms; a pyridylalkyl in which the alkyl group contains from 1 to 3 carbon atoms; a naphthylalkyl in which the alkyl group contains from 1 to 3 carbon atoms; a pyridylthioalkyl in which the alkyl group contains from 1 to 3 carbon atoms; a styryl; a 1-methylimidazol-2-ylthioalkyl in which the alkyl group contains from 1 to 3 carbon atoms; a 1-oxophenyl-3-indan-2-yl; or an unsubstituted or mono- or poly-substituted aromatic or heteroaromatic group;

or a salt thereof with a mineral or organic acid, wherein said stereoselective method comprises the steps of:

(1) treating a compound of the formula (XVII*)

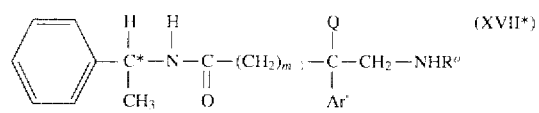

in which Q, Ar' and m are as defined above, and R° is hydrogen, a methyl group or a group $(CH_2)_n$—L°, in which n is as defined above, and L° is hydrogen or an amino group protected by an N-protecting group in a solvent, in an acid medium, to give the amino acid of the formula (XVIII*)

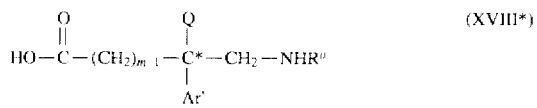

in which Q, Ar', m and R° are as defined above;

(2) esterifying said amino acid of the formula (XVIII*) in an alkanol, AlkOH, in which Alk is an alkyl having 1 to 4 carbon atoms, in an acid medium;

(3) treating the resultant ester of the formula

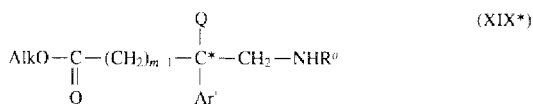

(XIX*) in which Alk, Q, m, Ar' and R° are as defined above, with either of (i) a functional derivative of an acid of the formula (III); or

(ii) an iso(thio)cyanate of the formula (III')

Z and W being as defined above;

(4) subjecting the resultant ester of the formula (XX*)

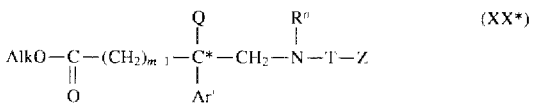

in which Alk, Ar', Q, m, T, Z and R° are as defined above, to the action of a reducing agent;

(5) converting the resultant alcohol of the formula (V*)

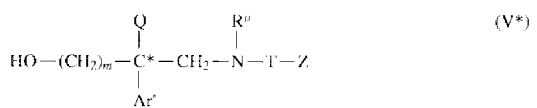 (V*)

in which m, Ar', Q, R°, T and Z are as defined above, into its methanesulfonate ester of the formula (VI*)

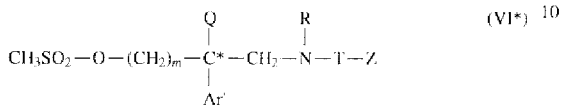 (VI*)

in which m, Ar', Q, R, T and Z are as defined above, and;

(6) treating said methanesulfonate ester with an amine of the formula (VII),

 (VII)

in which Ar, X, X' and Y are as defined above, and deprotecting, if appropriate, to give said compound of formula (I*).

* * * * *

UNITED STATES PATENT AND TRADEMARK OFFICE
CERTIFICATE OF CORRECTION

PATENT NO. : 5,618,938

DATED : April 8, 1997

INVENTOR(S) : Xavier EMONDS-ALT et al.

Page 1 of 2

It is certified that error appears in the above-indentified patent and that said Letters Patent is hereby corrected as shown below:

Column 74, line 14, after Claim 1, insert the following new claims:

--2. A method according to claim 1, wherein in the synthesis intermediates of formulae XVII*, XVIII*, XIX*, XX*, V*, and VI*, m = 2; Q = H; Ar' = 3, 4-dichlorophenyl; R° = H; and T - Z = 2,4-dichlorobenzoyl;

in the synthesis intermediate of formula (III), Z is a 2,4-dichlorophenyl; and in the synthesis intermediate of formula (VII); Ar is phenyl, X and X' are hydrogen atoms; and Y is -CH-.

UNITED STATES PATENT AND TRADEMARK OFFICE
CERTIFICATE OF CORRECTION

PATENT NO. : 5,618,938
DATED : April 8, 1997
INVENTOR(S) : Xavier EMONDS-ALT et al.

It is certified that error appears in the above-indentified patent and that said Letters Patent is hereby corrected as shown below:

3. A method according to claim 1, wherein in the synthesis intermediates of formulae XVII*, XVIII*, XIX*, XX*, V*, and VI*, m = 2; Q = H; Ar' = 3,4-difluorophenyl; R° = H; and T - Z = 2,4-dichlorobenzoyl;

in the synthesis intermediate of formula (III), Z is a 2,4-dichlorophenyl; and in the synthesis intermediate of formula (VII); Ar is phenyl, X and X' are hydrogen atoms; and Y is -CH-. --.

Signed and Sealed this

Ninth Day of December, 1997

Attest:

BRUCE LEHMAN

*Attesting Officer*      *Commissioner of Patents and Trademarks*